United States Patent [19]
Chang et al.

[11] Patent Number: 6,022,721
[45] Date of Patent: Feb. 8, 2000

[54] CATALASE, THE GENE THEREOF AND COMPOSITION COMPRISING THE SAME, AND PROCESS FOR PREPARING CATALASE USING GENETIC ENGINEERING TECHNOLOGY

[75] Inventors: Li-Yen Edward Chang; Ching-Long Hwong; Cheng-Kai Lo, all of Taipei, Taiwan

[73] Assignee: Development Center for Biotechnology, Taiwan

[21] Appl. No.: 09/027,166

[22] Filed: Feb. 20, 1998

[30] Foreign Application Priority Data

Jan. 3, 1997 [TW] Taiwan ................... 86100018
Dec. 11, 1997 [TW] Taiwan ................... 97120386

[51] Int. Cl.⁷ .............. C12N 9/08; C12N 15/53; C12N 15/63; C12N 15/70; A01N 37/18
[52] U.S. Cl. ............ 435/192; 435/69.1; 435/252.3; 435/252.33; 435/320.1; 536/23.2; 514/2
[58] Field of Search .................. 435/192, 69.1, 435/252.3, 252.33, 320.1; 514/2; 536/23.2

[56] References Cited

U.S. PATENT DOCUMENTS

| | | | |
|---|---|---|---|
| 2,635,069 | 4/1953 | Baker | 195/66 |
| 3,123,539 | 3/1964 | Beers, Jr. | 195/66 |
| 4,585,488 | 4/1986 | Giefer | 134/27 |
| 5,145,644 | 9/1992 | Park et al. | 422/28 |
| 5,360,732 | 11/1994 | Berka et al. | 435/192 |
| 5,362,647 | 11/1994 | Cook et al. | 435/264 |
| 5,521,091 | 5/1996 | Cook et al. | 435/264 |
| 5,571,719 | 11/1996 | Christensen et al. | 435/264 |
| 5,646,025 | 7/1997 | Moyer | 435/129 |
| 5,726,051 | 3/1998 | Fraij et al. | 435/193 |

FOREIGN PATENT DOCUMENTS

WO 93/17721  9/1993  WIPO.

OTHER PUBLICATIONS

Chang, R.–C., et al., Biochemical and Biophysical Research Communications, vol. 228, "Facile purification of highly active recombinant Staphylococcus hyicus lipase fragment and characterization of a putative Lid region", pp. 774–779, 1996.

Von Ossowski, I., et al., Journal of Bacteriology, vol. 173, "Nucleotide sequecne of *Escherichia coli* katE, which encodes catalase HPII", pp. 514–520, 1991.

Loprasert, S., et al., Journal of Bacteriology, vol. 171, "Cloning, nucleotide sequence, and expression in *Escherichia coli* of the *Bacillus stearothermophilus* peroxidase gene (perA)", pp. 4871–4875, 1989.

Bol, D. A., et al., Gene, vol. 109, "The isolation, cloning and identification of a vegetative catalase from *Bacillus subtilis*", pp. 31–37, 1991.

(List continued on next page.)

*Primary Examiner*—Ponnathapura Achutamurthy
*Assistant Examiner*—William W. Moore
*Attorney, Agent, or Firm*—McDonnell Boehnen Hulbert & Berghoff

[57] ABSTRACT

The invention provides a novel catalase which is cloned from *Bacillus theremoglucosidasius*. The invention further provides a process for preparing catalase in high yield, which comprises constructing expression vectors and transformant cells with catalase genes cloned from microorganisms using genetic engineering technology, and obtaining the expression product. The invention also provides a novel recombinant plasmid and a novel transformant cell constructed in the process.

In addition, the invention provides a composition for decomposing hydrogen peroxide contained in the residual disinfectant on contact lenses, which comprising the novel catalase of the invention.

19 Claims, 12 Drawing Sheets

OTHER PUBLICATIONS

Trakulnalmeanmsai, S., et al., Journal of Fermentation and Bioengineering, vol. 74, "Revised sequence and activity of *Bacillus stearothermophilus* catalase I (formerly peroxidase)", pp. 234–237, 1992.

Engelmann, S., et al., Journal of Bacteriology, vol. 177, "Cloning, nucleotide sequence, and regulation of katE encoding a sigmaB–dependent catalase in *Bacillus subtilis*", pp. 5598–5605, 1995.

Furuta and Hayashi (1990) Purification and properties of recombinant rat catalase produced in *Escherlchla coli*, J. Biochem 107:708–713.

```
   1 atgagttcaa ataaactgac aactagctgg ggcgctccgg ttggagataa
  51 tcaaaactca atgactgccg gttctcgcgg accaacttta attcaagatg
 101 tacatttact cgaaaaattg gcccatttca accgagaacg tgttcctgaa
 151 cgtgttgttc acgccaaagg agcaggcgca cacggatatt ttgaagtgac
 201 aaacgacgta acaaaataca cgaaagccgc tttcctttct gaagtcggca 251 aacgcacacc gttgttcatc cgtttctcaa cagttgccgg tgaacttggc
 301 tctgctgaca cagttcgcga cccgcgcgga tttgctgtta aattttatac
 351 tgaagaagga aactacgaca tcgtcggcaa caatacgcct gtattcttta
 401 tccgcgatgc gattaagttc cctgatttca tccatacaca aaaagagat
 451 ccaaaaacac acctgaaaaa ccctacggct gtatgggatt tctggtcact 501 ttcaccagag tcactgcacc aagtgacaat cctgatgtct gaccgcggaa
 551 ttcctgcgac acttcgccac atgcacggct cggaagcca tacattcaaa
 601 tggacaaatg ccgaacccga aggcgtatgg attaaatatc actttaaaac
 651 agaacaaggc gtgaaaaacc ttgatgtcaa tacggcagca aaaattgccg
 701 gtgaaaaccc tgattaccat acagaagacc ttttcaacgc aatcgaaaac 751 ggtgattatc ctgcatggaa actatatgtg caaatcatgc ctttagaaga
 801 tgcaaatacg taccgtttcg atccgtttga tgtcacaaaa gtttggtctc
 851 aaaaagacta cccgttaatc gaggtcggac gcatggttct agacagaaat
 901 ccggaaaact actttgcaga ggtagaacaa gcgacatttt cacctggaac
 951 cctcgtgcct ggtattgatg tttcaccgga taaaatgctt caaggtcgac 1001 ttttttgctta tcatgatgca caccgctacc gtgtcggtgc aaaccatcaa
1051 gcgctgccaa tcaaccgcgc acgcaacaaa gtaaacaatt atcagcgtga
1101 tgggcaaatg cgttttgatg ataacggcgg cggatctgtg tattacgagc
1151 ctaacagctt cggcggtcca aaagagtcac ctgaggataa gcaagcagca
1201 tatccggtac aaggtatcgc tgacagcgta agctacgatc actacgatca 1251 ctacactcaa gccggcgatc tgtatcgttt aatgagtgaa gatgaacgta
1301 cccgccttgt tgaaaatatc gttaatgcca tgaagccggt agaaaaagaa
1351 gaaatcaagc tgcgccaaat cgagcacttc tacaaagcgg atcctgaata
1401 cggaaaacgc gtggcagaag gccttggatt gccgattaaa aaagattctt
1451 aa
```

FIG. 2

```
          10         20         30         40         50         60
ATGAGTTCAA ATAAACTGAC AACTAGCTGG GGAGCACCTG TTGGCGATAA CCAAAACTCG 70         80         90        100        110        120
ATAACGGCCG GCAATCCTGG CCCGACATTA ATCCAAGACG TACATCTTAT CGAAAAATTA 130        140        150        160        170        180
GCACACTTCA ATAGAGAACG TGTCCCAGAA CGTGTTGTCC ATGCGAAAGG CGCTGGTGCG 190        200        210        220        230        240
CACGGCTATT TCGAAGTAAC AAACGATATG TCGAAATACA CAAAAGCGAA AGTGTTTAAC 250        260        270        280        290        300
GGTGTTGGCA AACGCACGCC TGTATTCGTC CGCTTCTCTA CTGTCGCCGG TGAATTGGGA 310        320        330        340        350        360
TCTGCGGATA CAGTCCGCGA CCCGCGCGGT TTTGCCGTCA AATTTTATAC CGAAGAAGGA 370        380        390        400        410        420
AACTATGACA TCGTTGGCAA CAACACACCG ATTTTCTTCA TTCGTGATGC GATTAAATTC 430        440        450        460        470        480
TCGGATTTTA TCCATACACA AAAACGCGAC CCGCGCACCC ATTTGATTTA TCCGACAGCA 490        500        510        520        530        540
ATGTGGGATT TCTTGTCTTT ATCTCCGGAA TCTTTGCACC AAGTCACTTA TTTATTCGGG 550        560        570        580        590        600
GATCGCGGCA TCCCATTGAC ATACCGCCAT ATGAACGGAT ACGGAAGCCA TACATTCAAA 610        620        630        640        650        660
TGGGTGAATG AAAAAGGCGA AGCGGTATGG GTAAAATACC ACTTTAAAAC AAACCAAGGC 670        680        690        700        710        720
GTGAAAAACA TGGATCCGGA ACTAGCGGTT AAAATCGCCG GAGAAAATCC GGATTACCAT 730        740        750        760        770        780
ACGGAAGATT TATATAACGC CATCGAAAAA GGCGACTATC CATCTTGGAC ATTATATGTG 790        800        810        820        830        840
CAAATTATGC CGTTAGAAGA CGCAAAAACA TACCGTTTCA ATCCATTTGA TGTCACAAAA 850        860        870        880        890        900
GTTTGGTCAC ATAAAGATTA TCCGTTAATT GAAGTCGGCC GTATGGTATT AAACCGCAAT
```

FIG. 5A

```
          910        920        930        940        950        960
CCAGAAAATT ATTTTGCCGA AGTCGAACAA GCGACATTCT CTCCTGGAAA CCTTGTTCCT 970        980        990       1000       1010       1020
GGCGTTGAAC CATCGCCGGA TAAAATCTTG CAAGCCCGTT TGTTCGCTTA TGCGGATGCG 1030       1040       1050       1060       1070       1080
CACCGTTACC GCGTCGGCGT GAACCATAAC TTGCTTCCGA TCAACCGCCC GCGCGTGGAA 1090       1100       1110       1120       1130       1140
GTAAACAATT ATCAACGTGA CGGCTTCATG CGCTTTGACA ATAATGGCGG CGGTTCGGTC 1150       1160       1170       1180       1190       1200
AACTACGAAC CAAACAGCTT CGGCGGACCG ACAGAAGTGC CAGAACATAA AACGACCCCA 1210       1220       1230       1240       1250       1260
TTCCCGGTAT CCGGCGTGGC AGAAAGCGTG CCATATGACG ACGATGATCA TTATACGCAA 1270       1280       1290       1300       1310       1320
GCAGGCGACT TATACCGTCT CATGAGCGAA GAAGAAAAAG CGCGCCTTGT GAAAACATT 1330       1340       1350       1360       1370       1380
GTCGAATCAT TGAAACAAGT AACAAAAGAA GAAATTAAAC TTCGCCAAAT CCGCCACTTC 1390       1400       1410       1420       1430       1440
TACAAAGCAG ACCCTGACTA CGGCCGCCGC GTTGCCGAAG GTCTTGGATT GCCGATTAAA 1450       1460       1470       1480       1490       1500
AAAGATTCT. .......... .......... .......... .......... ..........
```

FIG. 5B

```
         10         20         30         40         50         60
MSSNKLTTSW GAPVGDNQNS ITAGNPGPTL IQDVHLIEKL AHFNRERVPE RVVHAKGAGA 70         80         90        100        110        120
HGYFEVTNDM SKYTKAKVFN GVGKRTPVFV RFSTVAGELG SADTVRDPRG FAVKFYTEEG 130        140        150        160        170        180
NYDIVGNNTP IFFIRDAIKF SDFIHTQKRD PRTHLIYPTA MWDFLSLSPE SLHQVTYLFG 190        200        210        220        230        240
DRGIPLTYRH MNGYGSHTFK WVNEKGEAVW VKYHFKTNQG VKNMDPELAV KIAGENPDYH 250        260        270        280        290        300
TEDLYNAIEK GDYPSWTLYV QIMPLEDAKT YRFNPFDVTK VWSHKDYPLI EVGRMVLNRN 310        320        330        340        350        360
PENYFAEVEQ ATFSPGNLVP GVEPSPDKIL QARLFAYADA HRYRVGVNHN LLPINRPRVE 370        380        390        400        410        420
VNNYQRDGFM RFDNNGGGSV NYEPNSFGGP TEVPEHKTTP FPVSGVAESV PYDDDDHYTQ 430        440        450        460        470        480
AGDLYRLMSE EEKARLVKNI VESLKQVTKE EIKLRQIRHF YKADPDYGRR VAEGLGLPIK 490        500        510        520        530        540
KDS......  ..........  ..........  ..........  ..........  ..........
```

FIG. 6

```
   1 ctgcagcctt tctttaaaag agtcgaaagc caggctttta atatttaaat
  51 caccataatt actctgtatt aagtttgtag aaaacatctc ccgcctcata
 101 ttgttaacaa aattattatc tcatttaaat ctaagtcatt tacaatataa
 151 gtttaagagc gacgccacag gatgaactat caaaaatagc tcatcatgat
 201 tagcaaaact taaccatttt aaaataaata aacaattaaa gaaaaaagat 251 cacttattta tagcaataga tcgtcaaagg cagctttttg ttacaggtgg
 301 tttgaatgaa tgtagcaacg aaatacagaa tttcaggtca tgtaactccc
 351 ggcaaaccgg gaggtatgta atccttactc agtcacttcc ccttcctggc
 401 ggatctgatt tgcccaacgt tgggcagatt caggcacagt aaacgccggt
 451 gagcgcagaa atgactctcc catcagtaca aacgaacat atttgccacg 501 cagcatccag acatcacgaa acgaatccat ctttatcgca tgttctggcg
 551 gcgcgggttc cgtgcgtggg acatagctaa taatctggcg gttttgctgg
 601 cggagcggtt tcttcattac tggcttcact aaacgcatat taaaaatcag
 651 aaaaactgta gtttagccga tttagcccct gtacgtcccg ctttgcgtgt
 701 atttcataac accgtttcca gaatagtctc cgaagcggga tctggctggt 751 ggtctatagt tagagagttt tttgaccaaa acagcggccc tttcagtaat
 801 aaattaagga gacgagttca atgtcgcaac ataacgaaaa gaacccacat
 851 cagcaccagt caccactaca cgattccagc gaagcgaaac cggggatgga
 901 ctcactggca cctgaggacg gctctcatcg tccagcggct gaaccaacac
 951 cgccaggtgc acaacctacc gccccaggga gcctgaaagc ccctgatacg 1001 cgtaacgaaa aacttaattc tctggaagac gtacgcaaag gcagtgaaaa
1051 ttatgcgctg accactaatc agggcgtgcg catcgccgac gatcaaaact
1101 cactgcgtgc cggtagccgt ggtccaacgc tgctggaaga ttttattctg
1151 cgcgagaaaa tcacccactt tgaccatgag cgcattccgg aacgtattgt
1201 tcatgcacgc ggatcagccg ctcacggtta tttccagcca tataaaagct 1251 taagcgatat taccaaagcg gatttcctct cagatccgaa caaaatcacc
1301 ccagtatttg tacgtttctc taccgttcag ggtggtgctg gctctgctga
1351 taccgtgcgt gatatccgtg ctttgccac caagttctat accgaagagg
1401 gtatttttga cctcgttggc aataacacgc caatcttctt tatccaggat
1451 gcgcataaat tccccgattt tgttcatgcg gtaaaaccag aaccgcactg
```

FIG. 8A

```
1501 ggcaattcca caagggcaaa gtgcccacga tactttctgg gattatgttt
1551 ctctgcaacc tgaaactctg cacaacgtga tgtgggcgat gtcggatcgc
1601 ggcatccccc gcagttaccg caccatggaa ggcttcggta ttcacacctt
1651 ccgcctgatt aatgccgaag ggaaggcaac gtttgtacgt ttccactgga
1701 aaccactggc aggtaaagcc tcactcgttt gggatgaagc acaaaaactc 1751 accggacgtg acccggactt ccaccgccgc gagttgtggg aagccattga
1801 agcaggcgat tttccggaat acgaactggg cttccagttg attcctgaag
1851 aagatgaatt caagttcgac ttcgatcttc tcgatccaac caaacttatc
1901 ccggaagaac tggtgcccgt tcagcgtgtc ggcaaaatgg tgctcaatcg
1951 caacccggat aacttctttg ctgaaaacga acaggcggct ttccatcctg 2001 ggcatatcgt gccgggactg gacttcacca acgatccgct gttgcaggga
2051 cgtttgttct cctataccga tacacaaatc agtcgtcttg gtgggccgaa
2101 tttccatgag attccgatta accgtccgac ctgcccttac cataatttcc
2151 agcgtgacgg catgcatcgc atggggatcg acactaaccc ggcgaattac
2201 gaaccgaact cgattaacga taactggccg cgcgaaacac cgccggggcc 2251 gaaacgcggc ggttttgaat cataccagga gcgcgtggaa ggcaataaag
2301 ttcgcgagcg cagcccatcg tttggcgaat attattccca tccgcgtctg
2351 ttctggctaa gtcagacgcc atttgagcag cgccatattg tcgatggttt
2401 cagttttgag ttaagcaaag tcgttcgtcc gtatattcgt gagcgcgttg
2451 ttgaccagct ggcgcatatt gatctcactc tggcccaggc ggtggcgaaa 2501 aatctcggta tcgaactgac tgacgaccag ctgaatatca ccccacctcc
2551 ggacgtcaac ggtctgaaaa aggatccatc cttaagtttg tacgccattc
2601 ctgacggtga tgtgaaaggt cgcgtggtag cgattttact taatgatgaa
2651 gtgagatcgg cagaccttct ggccattctc aaggcgctga aggccaaagg
2701 cgttcatgcc aaactgctct actcccgaat gggtgaagtg actgcggatg 2751 acggaacggt gttgcctata gccgctacct ttgccggtgc accttcgctg
2801 acggtcgatg cggtcattgt cccttgcggc aatatcgcgg atatcgctga
2851 caacggcgat gccaactact acctgatgga agcctacaaa caccttaaac
2901 cgattgcgct ggcgggtgac gcgcgcaagt taaagcaac aatcaagatc
2951 gctgaccagg gtgaagaagg gattgtggaa gctgacagcg ctgacggtag 3001 ttttatggat gaactgctaa cgctgatggc agcacaccgc gtgtggtcac
3051 gcattcctaa gattgacaaa attcctgcct gatgggagcg cgcaattgcg
3101 ccgcctcaat gatttacata gtgcgctttg tttatgccgg atgcgcgtga
3151 acgccttatc cggcctacaa aactgtgcaa attcaatata ttgcaggaaa
3201 cacgtaggcc tgataagcga agccatcagg cagttttgcg tttgtcagca 3251 gtctcaagcg gcggcagtta cgccgccttt gtaggaatta atcgccggat
3301 gcaaggttca cgccgatctg gcaaacatcc tcacttacac atcccgataa
3351 ctccccaacc gataaccacg ctgagcgata gcacctttca acgacgctga
3401 tgtcaacaca tccagctccg ttaagcgtgg gaaacagtaa gcactctgac
3451 ggatagtatt atcgat
```

FIG. 8B

CATALASE, THE GENE THEREOF AND COMPOSITION COMPRISING THE SAME, AND PROCESS FOR PREPARING CATALASE USING GENETIC ENGINEERING TECHNOLOGY

FIELD OF THE INVENTION

The invention relates to a novel catalase, its use, and a process for preparing the catalase. Specifically, the invention provides a novel catalase cloned from *Bacillus theremoglucosidasius*, a composition comprising said catalase, and a process for preparing catalase in high yield which comprises using genetic engineering technology to clone catalase genes, constructing expression vectors, and transforming host cells.

BACKGROUND OF THE INVENTION

Hydrogen peroxide, which has germ-killing, cleaning, bleaching and disinfecting activities, is in general utilized in the disinfectant of contact lenses and in the bleaching agent of textile materials, and also recognized as a legal food additive. However, hydrogen peroxide is known to have the tendency to generate free oxygen having high reactivity, the strong oxidizing effect of which will cause proteins to denature. Hence, after the disinfecting operation of contact lenses or the bleaching procedure of textile materials using hydrogen peroxide, the residual hydrogen peroxide must be subsequently decomposed to avoid the undesired injury caused to users.

For this purpose, skilled artisans often use catalases to decompose hydrogen peroxide residues, which also is generally recognized as the most efficient method. For example, U.S. Pat. Nos. 4,585,488, 5,145,644, 5,362,647 and 5,521,091 disclose methods for the destruction of the hydrogen peroxide remaining in the disinfectant of contact lenses in which a catalase is added during the disinfecting operation. In addition, GB 2216149 and JP-A-104781 teach that, after bleached with hydrogen peroxide, textile substrates should be further treated with a catalase to destroy the hydrogen peroxide residues prior to the dyeing step.

Catalases [hydrogen peroxide oxidoreductases (EC 1.11.1.6)] are enzymes which catalyze the conversion of two molecules of hydrogen peroxide ($H_2O_2$) to one molecule of oxygen ($O_2$) through oxidation and two molecules of water ($H_2O$) through reduction. The catalysis reaction is as follows:

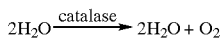

Catalases are present in certain animal, plant and microorganism cells, and are the required enzymes for these cells to survive in the aerobic environment. At present almost all the catalases available are obtained by purification from such cells, and among which the catalase derived from bovine livers, in particular, has been the most preferred one for the above mentioned purposes. However, in 1990, a chronic viral disease known as BSE (bovine spongiform encephalopathy) out-broke in European cattle herds. Recent studies have shown that human may be infected with this disease [Dellar and Lacey 1991 Nutr. Health (Bicester) 7:117–134; Dealler and Lacey 1990 Food Microbiol. 7:253–280). It arouses interests in finding non-mammalian-derived catalases, such as those derived from microorganism sources, instead of bovine liver catalases for the industrial applications.

Microorganisms which have been employed to obtain catalase preparations through fermentation include *Aspergillus niger*, *Penicillium notatutn*, *Micrococcus luteus*, etc. For instance, U.S. Pat. No. 3,123,539 discloses catalases derived from fungi such as *Aspergillus niger* and *Penicillium notatum*; U.S. Pat. No. 2,635,069 and 5,360,732 and WO 93/17721 disclose catalases generated from *Aspergillus niger*; and U.S. Pat. No. 5,521,091 discloses catalases derived from *Micrococcus luteus* and *Aspergillus niger*. The catalases taught in the above patents are prepared by conventional methods including fermenting microorganisms, breaking cell bodies, and then purifying crude extract.

Nevertheless, the yields of catalases prepared from such fermentation methods are not satisfactory. For example, U.S. Pat. No. 3,123,539 discloses that the 1000 g protein product recovered from the cell bodies of *Micrococcus luteus* (wet weight 95 pounds) yields only 5% of catalase; and U.S. Pat. No. 2,635,069 teaches that each gram crude protein extract obtained from the action of *Aspergillus niger* has only 2.4 units of catalase activity. For the sake of improving catalase yield, U.S. Pat. No. 5,360,732 tries to produce novel strains of *Aspergillus niger*, and the resulted catalytic activity is 14.17 units per milligram crude protein extract. According to the data shown in Table 1 of WO 93/17721, the specific activity of *Aspergillus niger* is about 7.5 units per microgram. It is calculated that the above 14.17 units of activity is performed by 1.9 μg catalase. In other words, the crude protein extract obtained in U.S. Pat. No. 5,360,732 contains less than 0.2% catalases.

Shuichi Furuta and Hiroaki Hayashi disclose in J. Biochem. 107:708–713 (1990) the expression of a recombinant catalase gene using genetic engineering technology. However, the produced catalase was not high in yield, merely 16 mg/4L before farther purification.

In view of the above, there continues to be a need for improving the catalase now employed in the art, both in its source and its preparation.

SUMMARY OF THE INVENTION

Accordingly, it is an object of the-invention to clone a novel catalase.

It is a further object of the invention to provide a process for preparing microorganism-derived catalase using genetic engineering technology. According to the process of the invention, the catalase not only could be obtained in high yield, but also could perform superior activity.

It is an another object of the invention to provide a novel recombinant plasmid and a novel transformant cell constructed during the process of the invention.

It is an additional object of the invention to provide a composition useful in decomposing hydrogen peroxide contained in the residual disinfectant remaining on contact lens, which comprises the novel catalase of the invention.

BRIEF DESCRIPTIONS OF THE DRAWINGS

FIG. 2 shows the DNA sequence of catalase kat 19 gene (SEQ ID NO:8).

FIG. 5 shows the DNA sequence of catalase kat TG gene (SEQ ID NO:6).

FIG. 6 shows the amino acid sequence of catalase TG (SEQ ID NO:7).

FIG. 8 shows the DNA sequence of catalase kat HPII gene (SEQ ID NO:20).

DETAILED DESCRIPTION OF THE INVENTION

Figure 1:
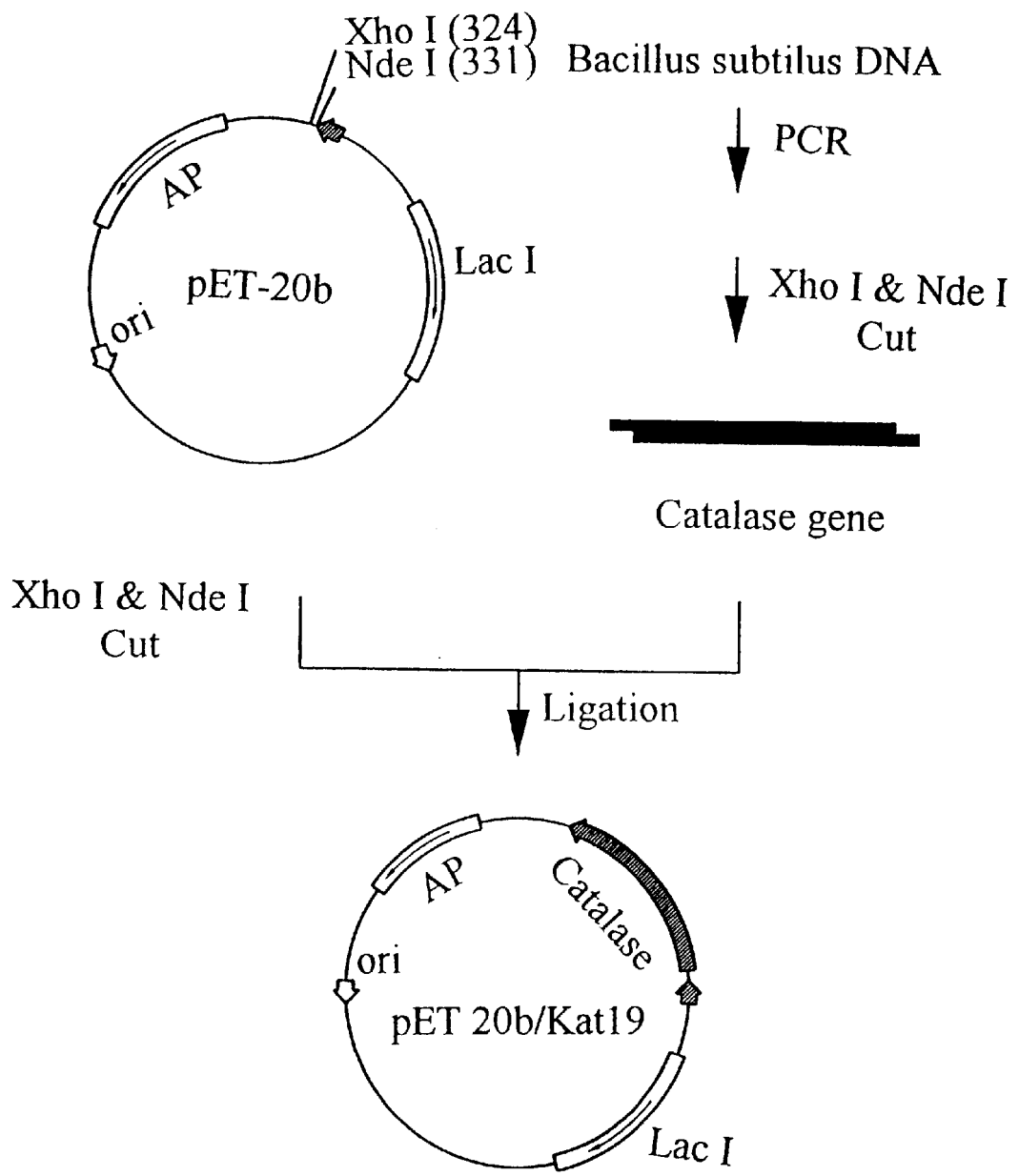
FIG. 1 shows the construction of expression plasmid pET 20b/kat 19.

While this specification concludes with claims particularly pointing out and distinctly claiming that which is considered to be the invention, it is believed that the invention can be better understood from a reading of the following detailed description of the invention and the appended examples.

The novel catalase gene of the invention is cloned from *Bacillus thermoglucosdasius*, using proper 5' and 3' primers synthesized from the 5' end and 3' end DNA sequences of the catalase gene of *Bacillus subtilis* (kat 19) disclosed in Bol and Yashin, Gene, 109:31–37 (1991). The resultant gene has been sequenced as listed in FIG. 5, with a similarity of 74.4% to kat 19 gene (SEQ ID NO:6). By inserting this gene into suitable expression vectors, transforming suitable host cells with the vectors and then expressing the gene in the host cells, the novel catalase of the invention can thus be obtained, having the amino acid as listed in FIG. 6 (SEQ ID NO:7). The novel catalase concerned by the invention has never been disclosed in any documents.

The invention also provides a process for preparing catalases using genetic engineering technology, said process comprising:

(a) constructing a recombinant plasmid by inserting the gene encoding said catalase into an expression vector containing a proper transcription promoter;

(b) transforming proper host cells with said recombinant plasmid;

(c) cultivating said transformant cells under the conditions suitable for the transformant cells to express the catalase gene; and (d) purifying the expressed catalase protein.

The novel process of the invention is not only useful in producing the new catalase mentioned above, but can be adopted to clone the catalases of other microorganism sources. In particular, the process of the invention comprises designing appropriate primers based on the DNA sequences of catalase genes of various microorganisms from the gene library, amplifying the catalase genes existing in the chromosomes of certain microorganisms with these primers, constructing expression vectors and transforming host cells with the vectors, and then expressing the genes so as to obtain the desired catalase.

The microorganisms useful in the invention can be any microorganisms possessing catalase genes, preferably bacteria. For example, the bacteria which may be employed in accordance with the invention to produce the novel catalase of the invention can be *Bacillus subtilis* (e.g. ATCC 6051, 6633), *Escherichia coli* DH5α, *Pseudomonas aeruginosa* (e.g. ATCC 29260), and *Bacillus thermoglucosdasius* (e.g. ATCC 43742). The microorganisms employed are not limited to any specific one but can be selected by persons skilled in the art according to their own requirements.

The amplification of catalase genes derived from microorganisms can be achieved using any conventional methods, such as potymerase chain reaction (PCR). The polymerase chain reaction has been a broadly-used technique for amplifying certain genes since 1980's (see, for example, U.S. Pat. No. 4,683,195 and 4,683,202), the protocol of which is as follows: First, the target nucleic acid is isolated from organism samples. Next, the double stranded target gene are denatured and annealed to the primers produced based on the sequences that flank the target gene. Then the amplification is carried out using polymerase in the presence of deoxynucleotide triphosphates in appropriate amounts. The necessary reaction parameters and reagents are well known to those skilled in the art. Although the polymerase chain reaction described above can be operated step by step, it is usually carried out with a commercial automatic machine (i.e. thermocycler).

The catalase genes obtained from amplification are then inserted into suitable expression vectors using conventional methods; said expression vectors include any vectors useful in bacteria, yeast, mammal or insect cell expression system, such as plasmids of pBR, pUC, pUB or pET series. Persons skilled in the art can adopt what they commonly use or choose a proper one according to their needs.

The expression vectors constructed are subsequently employed to transform proper host cells and then expressed therein. According to the present invention, the host cells which may be employed include, for example, bacterial cells (e.g. *E. coli* or *B. subtilis*), yeast cells (e.g. brewing yeast), mammal cells (e.g. mouse fiberblasts) and insect cells, preferably bacterial cells, and more preferably *E. coli* cells. The transformant cells are cultivated under conditions that facilitate the mass expression of the heterogenetic plasmid, and the desired protein product is then separated. In accordance with the invention, the crude protein extract would contain 15–50% active catalase. After purification by conventional methods such as histidine affinity chromatography or acetone precipitation, a catalase of 95% purity can be obtained.

The advantages of producing catalases according to the present process reside in not only its simple procedures and low cost, but its high production which is superior to that can be made by any conventional methods, such as fermentation. In addition, the produced catalase is surprisingly excellent in catalytic activities; therefore, it is very suitable for use in compositions for destroying hydrogen peroxide, especially compositions for removing the residual hydrogen peroxide remaining on contact lens.

In an aspect of the invention, compositions are provided which comprises the novel catalase of the invention to decompose the residual hydrogen peroxide remaining on contact lens.

The preparation of the compositions comprising the catalase product of the invention, as well as the formulations and application methods thereof, are all well known to skilled artisans. Reference can be referred to include e.g. U.S. Pat. No. 5,521,091, 5,362,647, 5,145,644 and 4,585,488. Such compositions may be formulated as solutions, or as solid forms including tablets, capsules, etc.

In one embodiment, the composition of the invention comprises an aqueous, substantially isotonic liquid medium containing the catalase of the invention. Such aqueous, substantially isotonic liquid medium preferably includes pH controlling effective amount of a conventional buffer component. More preferably, the buffer component is effective to control the pH of the liquid medium in the range of about 3 to about 10, for example, about 6 to about 8.

The amount of the catalase employed is preferably sufficient to destroy all hydrogen peroxide present in the hydrogen peroxide-containing medium on disinfected contact lens but not detrimental to lens per se and safe and comfortable wear. Typically, the catalase employed is preferably present in an amount of about 10 to about 1000, more preferably about 20 to about 800, International Units of catalase activity per milliliter of liquid medium.

In another embodiment of the invention, solid compositions which may be present in the form of tablets, capsules, one or more solid particles, and the like, are provided. Such solid compositions include a coated portion, e.g. a core, and a barrier or release delaying component. The coated portion or core includes the catalase of the invention. The barrier component (which may include water soluble vinyl polymers, such as polyvinylpyrollidone and polyvinyl alcohol; water soluble proteins; polysaccharides and cellulose derivatives, such as methyl cellulose) acts to delay, after the composition is initially contacted with the hydrogen peroxide-containing liquid medium, the release of the catalase into the medium for a period of time, preferably sufficient to allow the lens to be disinfected by the hydrogen peroxide. The detailed formulations of such compositions can be referred to the documents mentioned above.

The following non-limiting examples further illustrate the contents of the invention more specifically.

EXAMPLE 1

Construction of Expression Plasmid pET 20b/kat19

A. Extraction of Chromosomal DNA from *Bacillus subtilis*

Bacto-trypton (10 g), Bacto-yeast extract (5 g), and NaCl (10 g) were dissolved in 1 L of deionized water. The pH value of the solution was adjusted to 7.5 with 1N NaOH. After the solution was sterilized under high pressure and cooled the medium called Luria-Bertani (LB) medium was obtained. Supplementing the above medium with 2 mL of 50 mg/mL ampicillin LB/Amp medium was obtained.

*Bacillus subtilis* strain (ATCC 6051) was cultured with shaking at 37° C. in 3 mL of LB broth for 24 hours. The culture was centrifuged (5 krpm/min) for 15 minutes, washed once with water, and then centrifuged again. After the supernatant wvas removed, 0.75 mL of water was added to the samples, and then 0.75 mL of phenol was added for extraction. After 30 minutes, the extract was centrifuged (12 krpm) for 15 minutes, and extracted with 0.75 mL of phenol for 30 minutes after the lower layers was removed. The resulted extract was centrifuged (12 krpm) for 15 minutes, extracted with 0.75 mL of chloroform for 15 minutes after removing the phenol layer and centrifuged (12 krpm) again. The lower layer was removed, to the extract two volume of ethanol was added, and an additional centrifugation of 15 minutes was carried out (12 krpm). The DNA was then precipitated, washed once with 75% ethanol, and dissolved with TE buffer containing 10mM Tris-HCl, pH 7.5, and 1 mM EDTA.

B. Cloning of *Bacillus subtilis* Catalase Gene (kat-19)

Synthesis of 5' and 3' primers: On the basis of the 5' and 3' end sequences of the catalase gene of *Bacillus subtilis* YB 2003 disclosed in Bol. and Yashin, Gene 109: 31–37 (1991) (kat-19 gene, see FIG. 2), a 5' primer, NdeI-kat 19 (+) having the following DNA sequence (SEQ ID NO:1):

TT<u>CATATG</u>AGTTCAAATAAACTGACAACT (this sequence possessed the gene for NdeI restriction enzyme), and a 3' primer, kat 19-XhoI (−) having the following DNA sequence (SEQ ID NO:2):

TT<u>CTCGAG</u>TTAAGAATCTTTTTTAATCGGCAA (this sequence possessed the gene for XhoI restriction enzyme), were synthesized.

Polymerase chain reaction (PCR): 0.5 µg chromosomal DNA of *Bacillus subtilis* was added into a solution contained 10 µL of 2.5 mM dNTPs, 10 µL of 10×PC2 buffer (containing 50 µM Tris-HCl, pH 9.1, 16 mM ammonium sulfate, 3.5 mM MgCl$_2$ and 150 µg/mL BSA), 1.0 µL of 0.2 µg/mL 5' primer, 1.0 µL of 0.2 µg/mL 3' primer, 78 µl of water and 1.0 µL of 5 U/µL Klentaq (LA Technology Inc., USA), and then 50 µL of mineral oil was added. The reaction parameters of the thermocycler (Robocycler, STRATAGENE, USA) were set as follows: 94° C. for 1 minute, one cycle; 94°C. for 30 seconds, 54° C. for 1 minute, 72° C. for 1.5 minutes, and repeated 30 cycles of these three operations. After the polymerase chain reaction, the resulted product was purified using QIA quick Spin PCR purifying reagent kit (QIAGEN, Germany), and then eluted with 100 µL water. By the analysis based on 0.8% agarose gel electrophoresis and stained with ethidium bromide, the amplified product was identified as the desired DNA fragment which has the size previously expected, i.e. about 1.5 kb.

C. Construction of Expression Plasmid pET 20b/kat-19 (FIG. 1)

The PCR product was digested with restriction enzymes NdeI and XhoI, reacted at 37° C. for 3 hours, then separated by agarose gel electrophoresis, and a fragment of about 1.5 kb was obtained. The DNA fragment was eluted with electrophoresis, and subsequently purified using QIA quick Spin PCR purification kit. By the reaction with T4 DNA ligase at 16° C. for 16 hours, the purified DNA was inserted into the expression vector pET-20b (Novogen, USA), which was pre-digested with NdeI and XhoI restriction enzymes. After ligation, the reaction mixture was employed to transform DH5α competent cells, and the recombinant plasmid having a size larger than pET 20b was then screened out. By the analyses with restriction enzymes and DNA sequencing technique based on Sanger's method using Sequence Version 2.0 DNA sequencing kit (United States Biochemical) and T7 promoter sequence (SEQ ID NO:3) (ATTAATACGACTCACTATAGG) as a primer, it was confirmed that the cloned DNA fragment of 1.5 kb was the kat-19 aene and the construction of expression plasmid pET 20b/kat19 had thus been accomplished.

EXAMPLE 2

Figure 3:
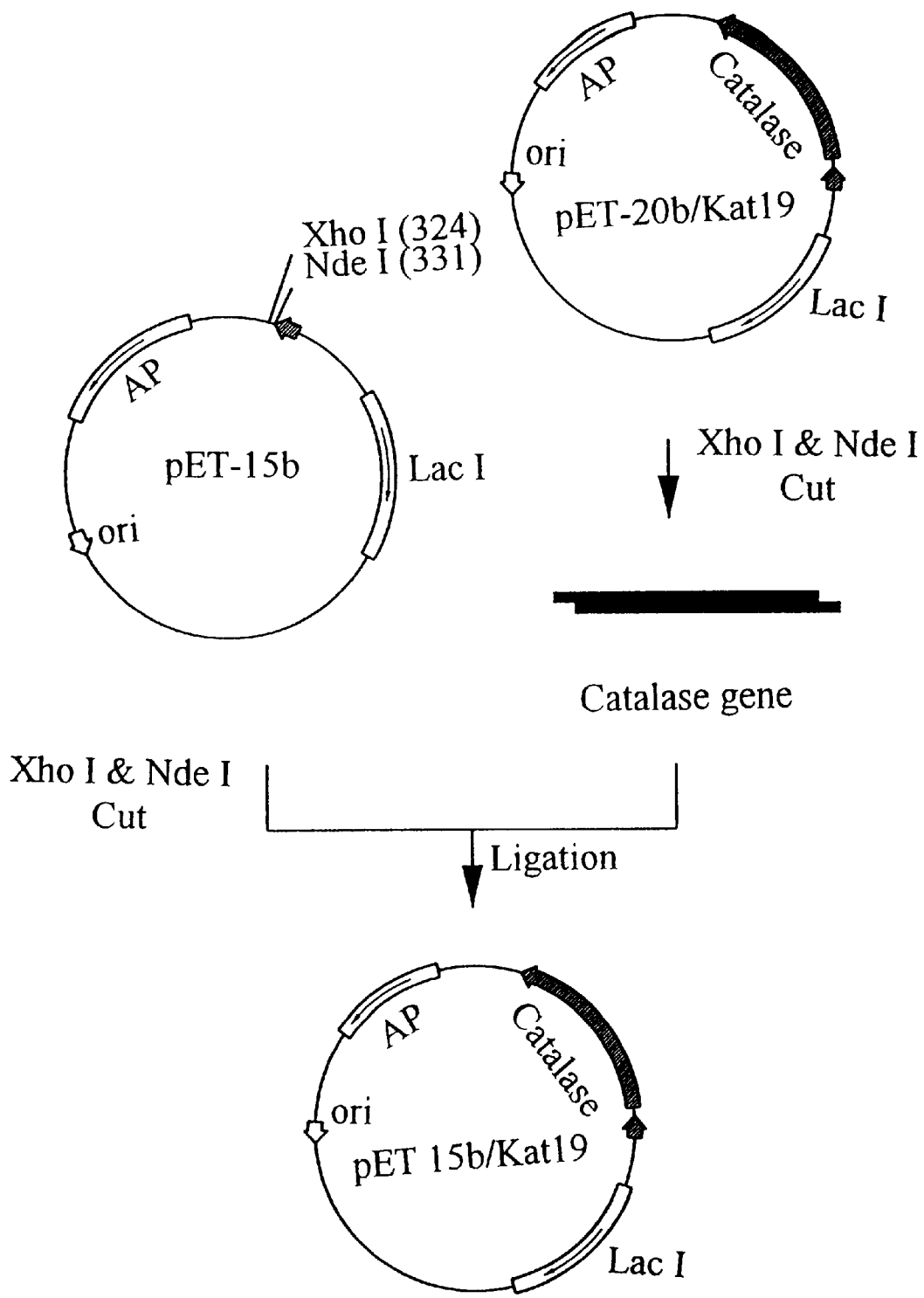
FIG. 3 shows the construction of expression plasmid pET 15b/kat 19.

Construction of Expression Plasmid pET 15b/kat19 (FIG. 3) The kat-19 gene was digested with restriction enzymes NdeI and XhoI, then separated by agarose gel electrophoresis, and a fragment of about 1.5 kb was obtained. The DNA fragment was eluted with electrophoresis, and purified using QIA quick Spin PCR purification kit. By the reaction with T4 DNA ligase at 16° C. for 16 hours, the purified DNA was ligated to the expression vector pET-15b that was pre-digested with NdeI and XhoI restriction enzymes, whereby the construction of the PET 15b/kat19 expression plasmid was accomplished. Using T7 promoter sequence as a primer to determine the 5' end DNA sequence, it was confirmed that the cloning of expression plasmid pET 15b/kat19 had been achieved.

EXAMPLE 3

Figure 4:
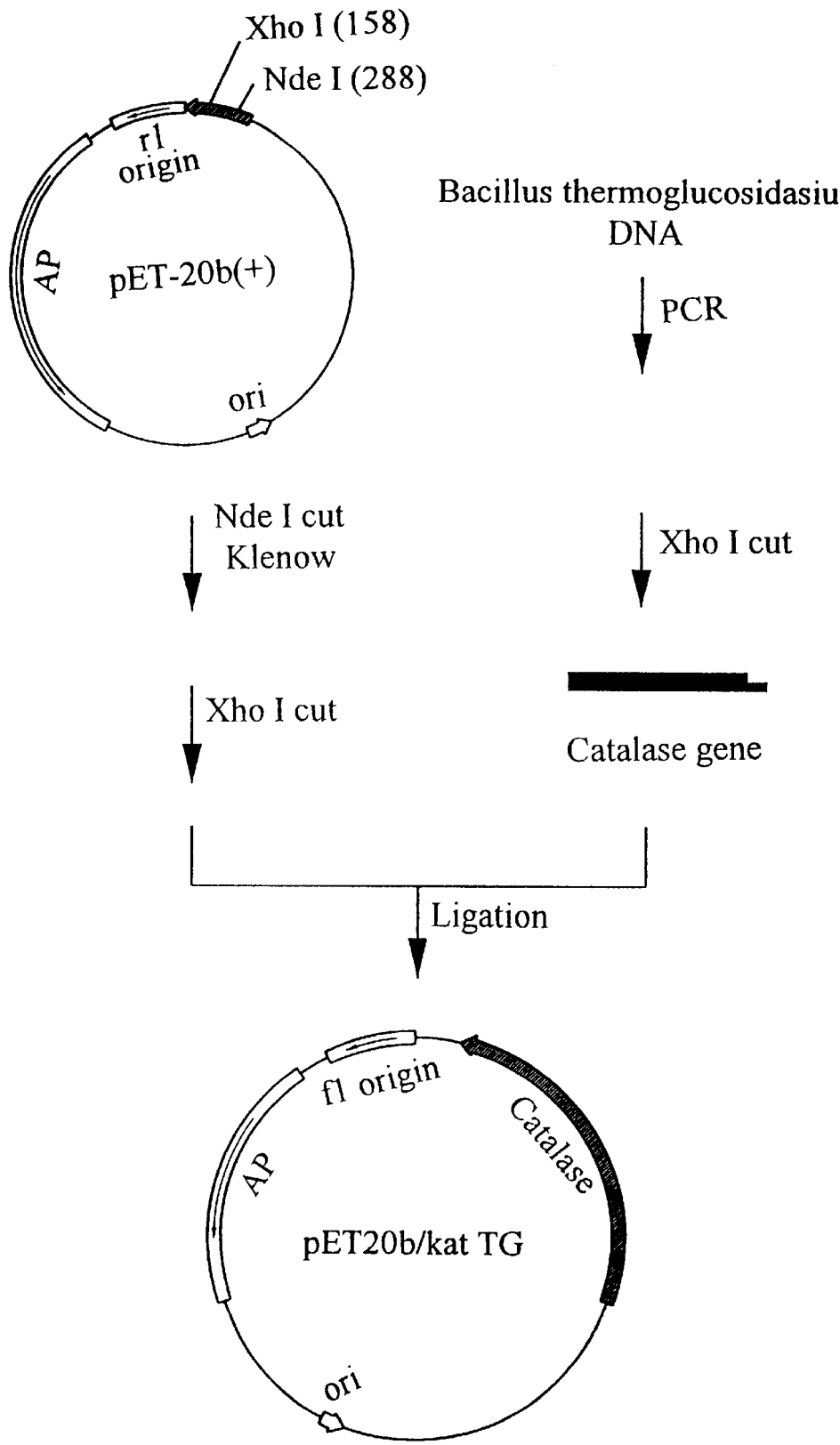
FIG. 4 shows the construction of expression plasmid pET 20b/kat TG.

Construction of Expression Plasmid pET 20b/katTG (FIG. 4)

The cells of *Bacillus thermoglucosdasius* (ATCC 43742) were cultivated at 55° C. and the chromosomal DNA was extracted from these bacterial cultures according to the method described in Example 1. To amplify the catalase gene of Bacillus thermoglucosdasins, the procedure is similar to Example 1 except the samplate was Bacillus thermoglucosdasins chromosomal DNA.

After polymerase chain reaction, a DNA fragment of 1.5 kb was obtained. The DNA fragment was purified, digested with XhoI restriction enzyme at 37° C. for 2 hours, purified again, and then stored at 4°C.

The expression vector pET 20b was digested with NdeI restriction enzyme at 37° C. for 2 hours, and treated with Klenow enzyme after purification. The vector was purified again and digested with XhoI restriction enzyme for 2 hours at 37° C. The DNA was separated using 0.8% agarose gel and a fragment of 3.7 kb was obtained, which was then eluted by electrophoresis and purified with QIA quick Spin PCR purification kit so as to produce the pET 20b vector useful in the following steps (in this vector, the NdeI site had been filled in and the XhoI site had been cut open). This vector was subsequently ligated to the above fragment of 1.5 kb, using T4 DNA ligase and incubated for 16 hours at 16° C., and the resulted vector was employed to transform DH5α competent cells. After screening procedures, an expression vector, pET 20b/kat TG, was obtained. Using the DNA sequence analysis based on Sanger's method with Sequence Version 2.0 DNA sequencing kit, it was found that the cloned DNA fragment (which DNA sequence is listed in FIG. 5) had a similarity to kat 19 gene of 74.4%. In addition, the protein product from translation of the DNA fragment (the amino acid sequence of which is listed in FIG. 6) was found to have a similarity of 81.0% to the vegetative catalase of *Bacillus subitlis*.

EXAMPLE 4

Figure 7:
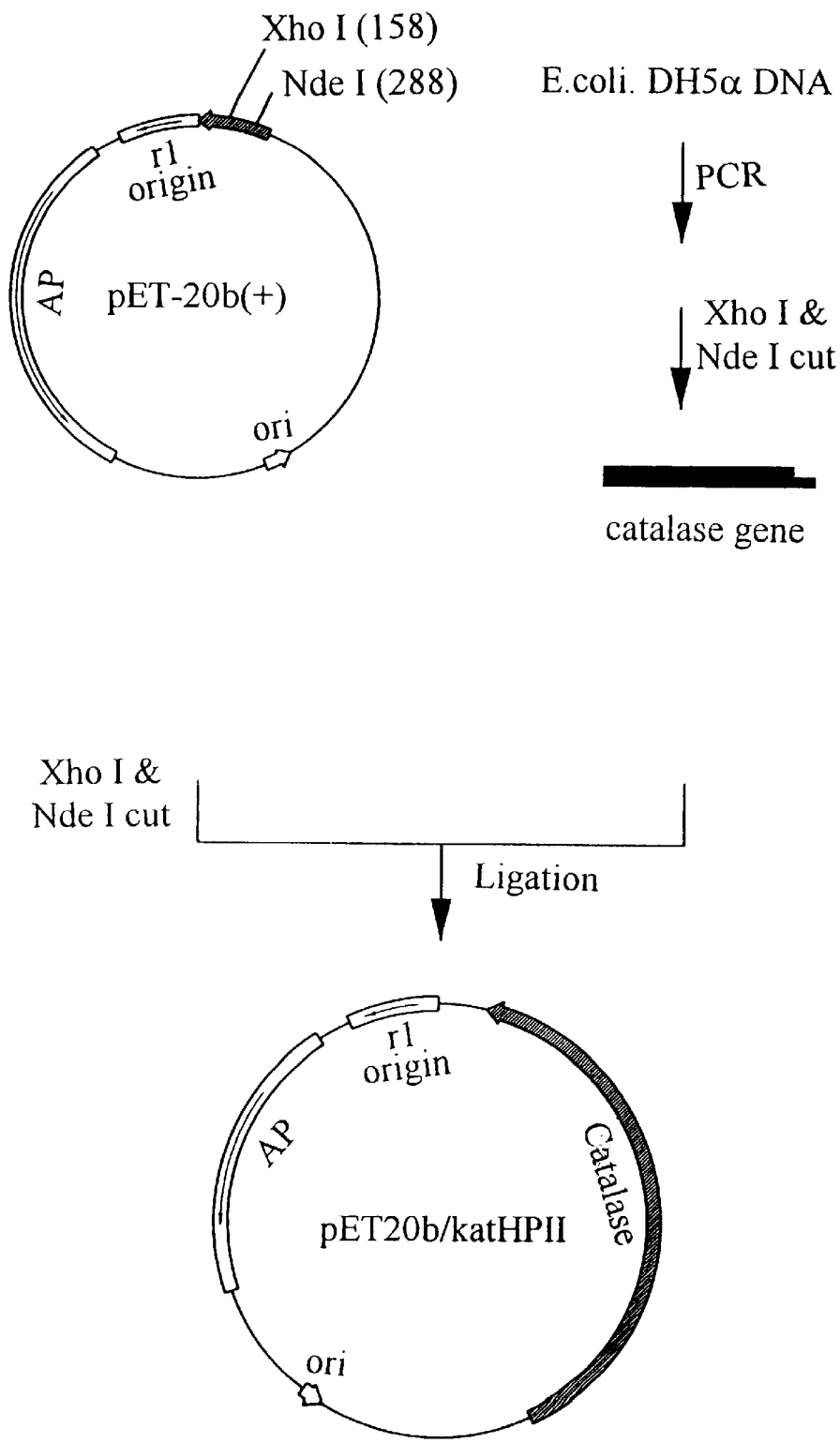
FIG. 7 shows the construction of expression plasmid pET 20b/kat HPII.

Construction of Expression Plasnid pET 20b/kat HPII (FIG. 7)

The chromosomal DNA of *E. coli* DH5α (GIBCO BRL, USA) was extracted according to the method described in Example 1. On the basis of the DNA sequence of *E. coli* HPII gene disclosed in J. Bacteriol 173: 514–520 (1991) (see FIG. 8), a 5' primer, NdeI-HPII (+) having the following DNA sequence (SEQ ID NO:4):

TCCCATATGTCGCAACATAACGAAAAGAAC (this sequence possessed the gene for the restriction enzyme NdeI), and a 3' primer, HPII-XhoI (−) having the followving DNA sequence (SEQ ID NO:5):

TTTCTCGAGGGCAGGAATTTTGTCAATCTTAGG (this sequence possessed the gene for the restriction enzyme XhoI), were synthesized. Using the chromosomal DNA of *E. coli* DH5α as the template, the HPII gene was amplified under the same PCR conditions set forth in Example 1 (except that the time for primer extension was 2 minutes). As the result, a DNA fragment of 2.0 kb (the expected size) was obtained.

The construction of expression plasmid pET 20b/kat HPII was carried out in the accordance with the method illustrated in Example 1. By the analysis using restriction enzymes and DNA sequencing techniques, it was confirmed that the cloned DNA fragment of 2.0 kb was HPII gene.

The above plasmids pET20b/kat19, pET15b/kat19, pET20b/HPII and pET20b/katTG were deposited with the American Type Culture Collection (ATCC), 12301 Parklawn Drive, Rockville, Md. 20852, USA, on Nov. 18 1997, under the Budapest Treaty, with the Accession Nos. ATCC 209467, 209469, 209470 and 209468 respectively.

EXAMPLE 5

Expression of Catalase

Figure 9:
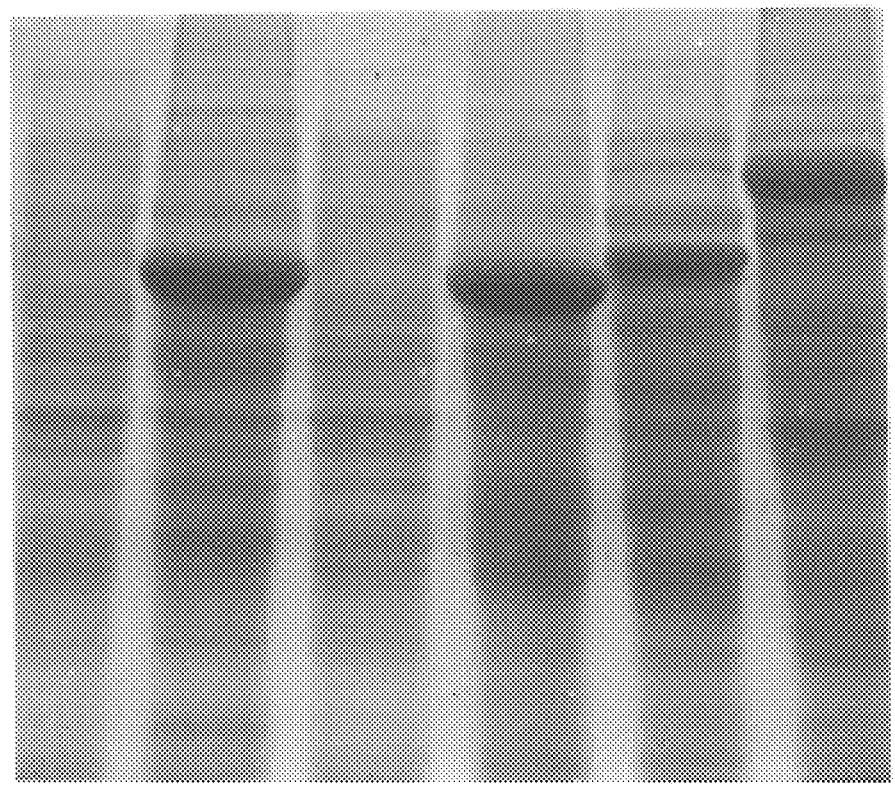
FIG. 9 shows the 12% polyacrylamide gel electrophoresis photograph of the catalases expressed by transformant strains. From left to right are the electrophoresis results of the catalases which are expressed by *E. coli* BL21 (DE3) strains transformed with pET15b, pET15b/kat19, pET 20b, pET 20b/kat19, pET 20b/kat TG and pET 20b/kat HPII, respectively.

The expression vectors pET 20b, pET 15b, pET 20b/kat 19, pET 20b/kat TG and pET 20b/kat HPII were employed to transform the cells of *E. coli* strain BL21 (DE3), and the bacteria were cultivated with shaking at 37° C. in 20 mL of LB/Amp medium until the O.D. 600 value had reached 2.0. To the cultures 0.1 mM isopropyl thio-β-galactoside (IPTG) was added to induce the expression of catalase. After 24 hours, the bacteria were collected. Centrifugation of 1.5 mL of each of the harvested bacterial suspensions was done and the supernatant was then removed. To the suspensions, 150 μL of 50 mM sodium phosphate buffer (pH 6.0) was first added and then 150 μL of 2× electrophoresis protein dyes containing 0.1M dithiothreitol, 2% SDS, 0.08M Tris-Cl, 15% glycerol and 0.06% bromphenol blue followed. The mixtures were heated at 95° C. for 5 minutes and then centrifuged for 5 minutes (12 krpm). The 12% SDS-PAGE analysis of 20 μL of each of the supemants obtained was subsequently carried out to analyze all the proteins present in the bacteria. The results are shown in FIG. 9; from left to right are the electrophoresis results of the catalases expressed by *E.coli* BL21 (DE3) strains transformed with pET 15b, pET 15b/kat 19, pET 20b, pET 20b/kat19, pET 20b/kat TG and pET 20b/kat HPII, respectively. According to FIG. 9, in the bacteria, there are approximately 15–50% of the total protein contained catalases. In other words, such host cells carrying catalase-expressing vectors could all produce catalases in very high yield.

EXAMPLE 6

Purification of Catalase

The cells of BL 21 (DE3) (Novogen, USA) strain transformed with expression vectors pET 20b/kat 19 were inoculated on 100 mL of LB/Amp medium, and cultivated with shaking at 37°C. till O.D. 600=2.0. After induction with 0.1M IPTG, the cultures were centrifuged and the medium were removed. The bacterial cells were resuspended in 10 mL of 50 mM sodium phosphate buffer (pH 6.4) and disrupted by sonication. After centrifugation for 15 minutes (12 krpm), the bacterial debris was precipitated and the supernatant was collected. The supernatant was mixed with an equivalent amount of acetone (added at 4° C.) for 30 minutes, centrifuged and the supernatant was removed. The precipitate obtained was dissolved in 10 mL of 50 mM sodium phosphate buffer, pH 6.4, stored at 4° C. for 12 hours, and subjected to centrifugation for 5 minutes (5 krpm). The supernant obtained from the centrifugation was collected so as to complete the purification procedure.

On the other hand, the cells of BL 21 (DE3) strain carrying expression vectors pET 15b/kat 19, pET 20b/kat TG and pET 20b/kat HPII were individually inocultated on 100 mL of LB/Amp medium, and cultivated with shaking at 37°C. When the O.D. 600 value had reached 2.0, 0.1M IPTG was added and the cultivation continued for additional 24 hours. The cultures were subjected to centrifugation followed by removing the medium, and then 20 mL of IMAC-5 containing 20 mM Tric-HCl (pH 7.9), 0.5M NaCl, 10% glycerol and 5 mM imidazole was added to resuspend the bacteria. The bacterial cells were then disrupted by sonication. After centrifugation, the bacterial debris was precipitated and the supernatant obtained was collected. The purification of catalases was done using 2.5 mL of histidine affinity chromatographic column (His-Bind resin, Novogen), according to the protocol suggested by Novogen (pET His. Tog$^{TG}$ System Protocols, Novogen).

The amount and the activity of the purified protein were measured as follows: The protein amount was determined by the reagents and procedures for protein quantitative analysis from Bio-RAD Co., using bovine serum albumin as a standard. The catalase activity was determined by measurement of OD value, under the UV light of 240 nm wavelength, the decomposed rate of hydrogen peroxide present in 50 mM sodium phosphate buffer (pH 7.0, 25° C.) from the reaction of the catalase obtained above. The initial concentration of hydrogen peroxide contained in the buffer was 20 mM, and the measurement interval was 20 seconds. Each unit (U) of catalase activity is defined as 1 μmol of hydrogen peroxide decomposed in 1 minute.

Figure 10:
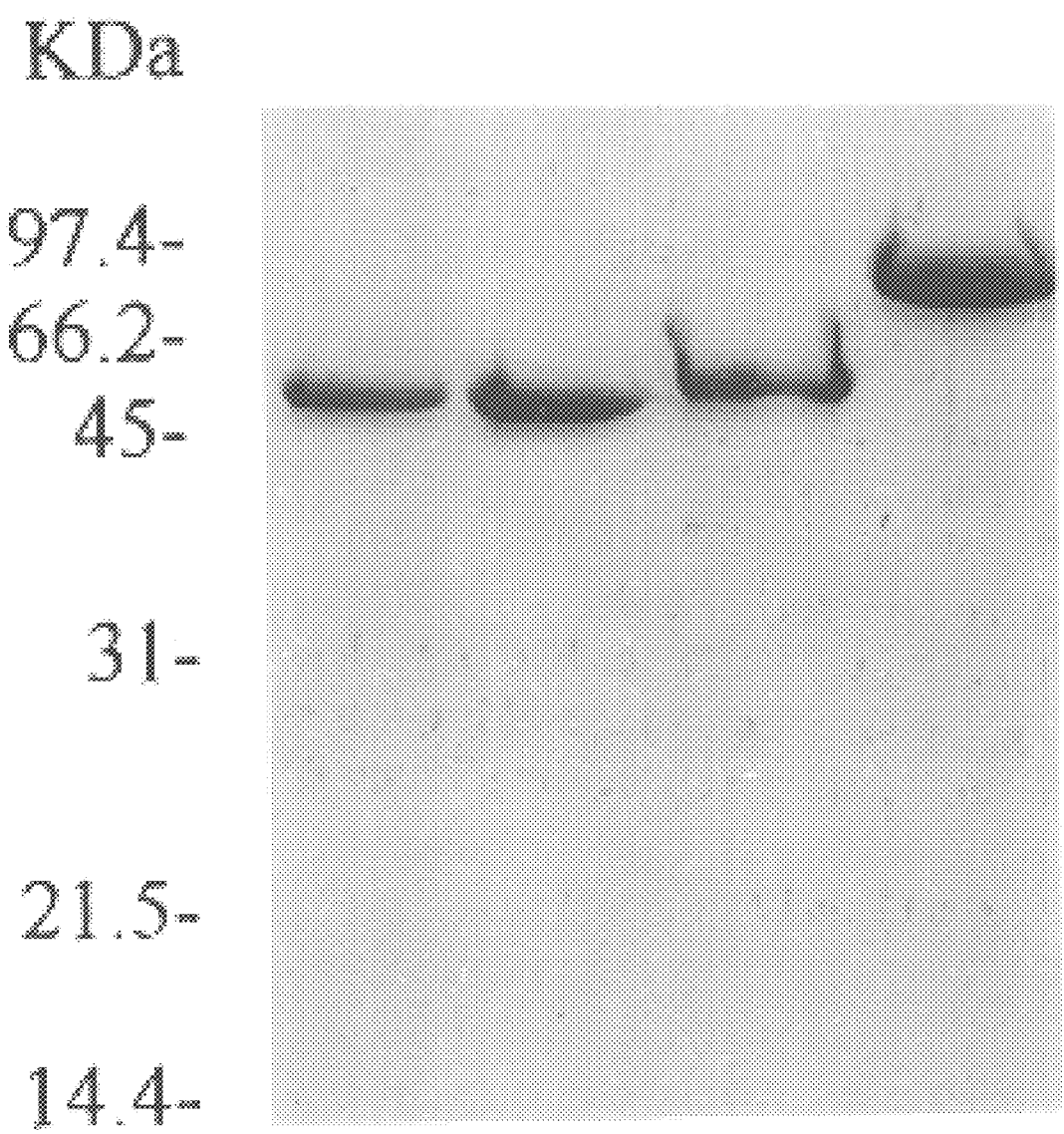
FIG. 10 shows the 12% polyacrylamide gel electrophoresis photograph of the catalases expressed by trans formant strains after purification. From left to right are the electrophoresis results of the purified catalases which are expressed by *E.coli* BL21 (DE3) strains transformed with pET 15b/kat 19, pET 20b/kat19, pET 20b/kat TG and pET 20b/kat HPII, respectively.

The measurement of the amounts and the activities of various catalases was performed according to the methods described above. In addition, the purity of the catalases (using 5 μg for each catalase) was determined by 12% polyacrylamide gel electrophoresis analysis. The results are shown in FIG. 10. From left to right are the protein standard, the catalases expressed by expression vectors pET 15b/kat 19, pET 20b/kat19, pET 20b/kat TG and pET 20b/kat HPII, respectively. The electrophoresis results indicate that all proteins have a purity higher than 95%. The specific activities of such catalases are listed as follows:

| Expression vectors | Specific activity (U/μg) |
|---|---|
| pET 15b/kat 19 | 18–22 |
| pET 20b/kat 19 | 18–22 |
| pET 20b/kat TG | 30–40 |
| pET 20b/kat HPII | 10–14 |

From the above table, it is recognized that all the catalases prepared according to the invention have superior catalytic activities. In addition, the specific activities of these catalases are all better than commercialized catalases derived from *Aspergillus niger* (about 5 U/μg according to the Merck catalog, and about 4–8 U/μg according to the Sigma catalog).

EXAMPLE 7

Decomposition Effect on Hydrogen Peroxide Present in Contact Lens Disinfectant

A commercialized contact lend disinfectant typically contains about 3%(w/v) hydrogen peroxide. The disinfection procedures are as follows: The contact lens to be disinfected were placed in 10 mL of 3% (w/v) aqueous solution of hydrogen peroxide for approximately 20 minutes. Afterward, the disinfected contact lens were removed from the hydrogen peroxide solution and placed in 10 mL of an aqueous solution containing a catalase, or alternatively, a catalase is added directly into the hydrogen peroxide solution. After about 10–20 minutes, the disinfected contact lens were removed from the solution, rinsed in saline solution and placed into the wearer's eye. To test the performance of the catalase of the invention in decomposing the hydrogen peroxide contained in the disinfectant for contact lens, a quantity, 50 μg, of each of the catalases prepared according to the example 6 were added into a 3% aqueous solution of hydrogen peroxide. It wvas found that the concerned catalases took only 5 minutes to destroy the hydrogen peroxide effectively, causing its concentration lower than 0.02% (w/v). Apparently, the efficacy of the catalase of the invention is superior to that of the commercialized product available.

EXAMPLE 8

Solid Composition

A layered tablet which has a core surrounded by a delayed release layer is prepared. The layered tablet has the following composition:

| Core | |
|---|---|
| Sodium Chloride | 89.4 mg |
| Dibasic Sodium Phosphate (Anhydrous) | 12.5 mg |
| Monobasic Sodium Phosphate Monohydrate (Anhydrous) | 0.87 mg |
| Polyethylene Glycol (M.W. 3350) | 1.05 mg |
| Lyophilized Catalase of the Invention | 2500 International Units |
| Coating Layer | |
| Hydroxypropylmethylcellulose | 8 mg |

EXAMPLE 9

Solution Composition

A two unit dose (10 mL) formulation is prepared and has the following composition:

| | |
|---|---|
| Sodium Chloride | 0.85% |
| Dibasic Sodium Phosphate heptahydrate | 0.402% |
| Monobasic Sodium Phosphate Monohydrate | 0.091% |
| Disodium Edetate | 0.100% |
| Liquid Catalase of The Invention[1] | 260 International Units/mL |
| Purified Water | QS-ad |

[1]The liquid catalase include 35–40% wt glycerol and 10% wt ethanol.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
       (A) LENGTH: 29 base pairs
       (B) TYPE: nucleic acid
       (C) STRANDEDNESS: single
       (D) TOPOLOGY: Not Relevant (ii) MOLECULE TYPE: other nucleic acid
       (A) DESCRIPTION: /desc = "5' primer"

(xi) SEQUENCE DESCRIPTION: SEQ ID NO:1:

TTCATATGAG TTCAAATAAA CTGACAACT                              29

SEQUENCE LISTING (1) GENERAL INFORMATION:                                     1

(i) APPLICANT: CHANG, Li-Yen Edward
               HWONG, Ching-Long

LO, Cheng-Kai (ii) TITLE OF INVENTION: Novel Catalase, The Gene Thereof and
           Composition Comprising The Same, And Process For Preparing Catalase Using Genetic Engineering Technology (iii) NUMBER OF SEQUENCES: 10

(iv) CORRESPONDENCE ADDRESS:
           (A) ADDRESSEE: McDonnell Boehnen Hulbert & Berghoff
           (B) STREET: 300 S. Wacker Drive Suite 3200          3003200
           (C) CITY: Chicago
           (D) STATE: IL
           (E) COUNTRY: USA
           (F) ZIP: 60606                                        60606

(v) COMPUTER READABLE FORM:
       (A) MEDIUM TYPE: Floppy disk
       (B) COMPUTER: IBM PC compatible
       (C) OPERATING SYSTEM: PC-DOS/MS-DOS
       (D) SOFTWARE: PatentIn Release #1.0, Version #1.30       10130

(vi) CURRENT APPLICATION DATA:
           (A) APPLICATION NUMBER:US/09/027,166
           (B) FILING DATE: 20-FEB-1998                         201998
           (C) CLASSIFICATION:435

(vii) PRIOR APPLICATION DATA:
           (A) APPLICATION NUMBER: TW 86100018                86100018
           (B) FILING DATE: 03-JAN-1997                         031997

(vii) PRIOR APPLICATION DATA:
           (A) APPLICATION NUMBER: CN 97120386.5             971203865
           (B) FILING DATE: 11-DEC-1997                         111997

(viii) ATTORNEY/AGENT INFORMATION:
           (A) NAME: CHAO, Mark
           (B) REGISTRATION NUMBER: 37,293                       37293
           (C) REFERENCE/DOCKET NUMBER: 98,180                   98180

(ix) TELECOMMUNICATION INFORMATION:
           (A) TELEPHONE: (312) 913-0001                    3129130001
           (B) TELEFAX: (312) 913-0002                      3129130002

(2) INFORMATION FOR SEQ ID NO:1:

```
    (i) SEQUENCE CHARACTERISTICS:
        (A) LENGTH: 29 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "5' primer"

(xi) SEQUENCE DESCRIPTION: SEQ ID NO:1:

TTCATATGAG TTCAAATAAA CTGACAACT                              29

(2) INFORMATION FOR SEQ ID NO:2:

(i) SEQUENCE CHARACTERISTICS:
        (A) LENGTH: 32 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "3' PRIMER"

(xi) SEQUENCE DESCRIPTION: SEQ ID NO:2:

TTCTCGAGTT AAGAATCTTT TTTAATCGGC AA                          32

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "T7 PROMOTER"

(xi) SEQUENCE DESCRIPTION: SEQ ID NO:3:

ATTAATACGA CTCACTATAG G                                      21

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "5' PRIMER"

(xi) SEQUENCE DESCRIPTION: SEQ ID NO:4:

TCCCATATGT CGCAACATAA CGAAAAGAAC                             30

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: Not Relevant (ii) MOLECULE TYPE: other nucleic acid
        (A) DESCRIPTION: /desc = "3' PRIMER"

(xi) SEQUENCE DESCRIPTION: SEQ ID NO:5:

TTTCTCGAGG GCAGGAATTT TGTCAATCTT AGG                         33

(2) INFORMATION FOR SEQ ID NO:6:
```

(i) SEQUENCE CHARACTERISTICS:
  (A) LENGTH: 1449 base pairs
  (B) TYPE: nucleic acid
  (C) STRANDEDNESS: single
  (D) TOPOLOGY: Not Relevant (ii) MOLECULE TYPE: cDNA (ix) FEATURE:
  (A) NAME/KEY: CDS
  (B) LOCATION: 1..1449

(ix) FEATURE:
  (A) NAME/KEY: mat_peptide
  (B) LOCATION: 1..1449

(xi) SEQUENCE DESCRIPTION: SEQ ID NO:6:

```
ATG AGT TCA AAT AAA CTG ACA ACT AGC TGG GGA GCA CCT GTT GGC GAT      48
Met Ser Ser Asn Lys Leu Thr Thr Ser Trp Gly Ala Pro Val Gly Asp
 1               5                  10                  15

AAC CAA AAC TCG ATA ACG GCC GGC AAT CCT GGC CCG ACA TTA ATC CAA      96
Asn Gln Asn Ser Ile Thr Ala Gly Asn Pro Gly Pro Thr Leu Ile Gln
             20                  25                  30

GAC GTA CAT CTT ATC GAA AAA TTA GCA CAC TTC AAT AGA GAA CGT GTC     144
Asp Val His Leu Ile Glu Lys Leu Ala His Phe Asn Arg Glu Arg Val
         35                  40                  45

CCA GAA CGT GTT GTC CAT GCG AAA GGC GCT GGT GCG CAC GGC TAT TTC     192
Pro Glu Arg Val Val His Ala Lys Gly Ala Gly Ala His Gly Tyr Phe
     50                  55                  60

GAA GTA ACA AAC GAT ATG TCG AAA TAC ACA AAA GCG AAA GTG TTT AAC     240
Glu Val Thr Asn Asp Met Ser Lys Tyr Thr Lys Ala Lys Val Phe Asn
 65                  70                  75                  80

GGT GTT GGC AAA CGC ACG CCT GTA TTC GTC CGC TTC TCT ACT GTC GCC     288
Gly Val Gly Lys Arg Thr Pro Val Phe Val Arg Phe Ser Thr Val Ala
                 85                  90                  95

GGT GAA TTG GGA TCT GCG GAT ACA GTC CGC GAC CCG CGC GGT TTT GCC     336
Gly Glu Leu Gly Ser Ala Asp Thr Val Arg Asp Pro Arg Gly Phe Ala
            100                 105                 110

GTC AAA TTT TAT ACC GAA GAA GGA AAC TAT GAC ATC GTT GGC AAC AAC     384
Val Lys Phe Tyr Thr Glu Glu Gly Asn Tyr Asp Ile Val Gly Asn Asn
        115                 120                 125

ACA CCG ATT TTC TTC ATT CGT GAT GCG ATT AAA TTC TCG GAT TTT ATC     432
Thr Pro Ile Phe Phe Ile Arg Asp Ala Ile Lys Phe Ser Asp Phe Ile
    130                 135                 140

CAT ACA CAA AAA CGC GAC CCG CGC ACC CAT TTG ATT TAT CCG ACA GCA     480
His Thr Gln Lys Arg Asp Pro Arg Thr His Leu Ile Tyr Pro Thr Ala
145                 150                 155                 160

ATG TGG GAT TTC TTG TCT TTA TCT CCG GAA TCT TTG CAC CAA GTC ACT     528
Met Trp Asp Phe Leu Ser Leu Ser Pro Glu Ser Leu His Gln Val Thr
                165                 170                 175

TAT TTA TTC GGG GAT CGC GGC ATC CCA TTG ACA TAC CGC CAT ATG AAC     576
Tyr Leu Phe Gly Asp Arg Gly Ile Pro Leu Thr Tyr Arg His Met Asn
            180                 185                 190

GGA TAC GGA AGC CAT ACA TTC AAA TGG GTG AAT GAA AAA GGC GAA GCG     624
Gly Tyr Gly Ser His Thr Phe Lys Trp Val Asn Glu Lys Gly Glu Ala
        195                 200                 205

GTA TGG GTA AAA TAC CAC TTT AAA ACA AAC CAA GGC GTG AAA AAC ATG     672
Val Trp Val Lys Tyr His Phe Lys Thr Asn Gln Gly Val Lys Asn Met
    210                 215                 220

GAT CCG GAA CTA GCG GTT AAA ATC GCC GGA GAA AAT CCG GAT TAC CAT     720
Asp Pro Glu Leu Ala Val Lys Ile Ala Gly Glu Asn Pro Asp Tyr His
225                 230                 235                 240
```

```
ACG GAA GAT TTA TAT AAC GCC ATC GAA AAA GGC GAC TAT CCA TCT TGG        768
Thr Glu Asp Leu Tyr Asn Ala Ile Glu Lys Gly Asp Tyr Pro Ser Trp
                245                 250                 255

ACA TTA TAT GTG CAA ATT ATG CCG TTA GAA GAC GCA AAA ACA TAC CGT        816
Thr Leu Tyr Val Gln Ile Met Pro Leu Glu Asp Ala Lys Thr Tyr Arg
                260                 265                 270

TTC AAT CCA TTT GAT GTC ACA AAA GTT TGG TCA CAT AAA GAT TAT CCG        864
Phe Asn Pro Phe Asp Val Thr Lys Val Trp Ser His Lys Asp Tyr Pro
                275                 280                 285

TTA ATT GAA GTC GGC CGT ATG GTA TTA AAC CGC AAT CCA GAA AAT TAT        912
Leu Ile Glu Val Gly Arg Met Val Leu Asn Arg Asn Pro Glu Asn Tyr
        290                 295                 300

TTT GCC GAA GTC GAA CAA GCG ACA TTC TCT CCT GGA AAC CTT GTT CCT        960
Phe Ala Glu Val Glu Gln Ala Thr Phe Ser Pro Gly Asn Leu Val Pro
305                 310                 315                 320

GGC GTT GAA CCA TCG CCG GAT AAA ATC TTG CAA GCC CGT TTG TTC GCT       1008
Gly Val Glu Pro Ser Pro Asp Lys Ile Leu Gln Ala Arg Leu Phe Ala
                325                 330                 335

TAT GCG GAT GCG CAC CGT TAC CGC GTC GGC GTG AAC CAT AAC TTG CTT       1056
Tyr Ala Asp Ala His Arg Tyr Arg Val Gly Val Asn His Asn Leu Leu
                340                 345                 350

CCG ATC AAC CGC CCG CGC GTG GAA GTA AAC AAT TAT CAA CGT GAC GGC       1104
Pro Ile Asn Arg Pro Arg Val Glu Val Asn Asn Tyr Gln Arg Asp Gly
                355                 360                 365

TTC ATG CGC TTT GAC AAT AAT GGC GGC GGT TCG GTC AAC TAC GAA CCA       1152
Phe Met Arg Phe Asp Asn Asn Gly Gly Gly Ser Val Asn Tyr Glu Pro
        370                 375                 380

AAC AGC TTC GGC GGA CCG ACA GAA GTG CCA GAA CAT AAA ACG ACC CCA       1200
Asn Ser Phe Gly Gly Pro Thr Glu Val Pro Glu His Lys Thr Thr Pro
385                 390                 395                 400

TTC CCG GTA TCC GGC GTG GCA GAA AGC GTG CCA TAT GAC GAC GAT GAT       1248
Phe Pro Val Ser Gly Val Ala Glu Ser Val Pro Tyr Asp Asp Asp Asp
                405                 410                 415

CAT TAT ACG CAA GCA GGC GAC TTA TAC CGT CTC ATG AGC GAA GAA GAA       1296
His Tyr Thr Gln Ala Gly Asp Leu Tyr Arg Leu Met Ser Glu Glu Glu
                420                 425                 430

AAA GCG CGC CTT GTG AAA AAC ATT GTC GAA TCA TTG AAA CAA GTA ACA       1344
Lys Ala Arg Leu Val Lys Asn Ile Val Glu Ser Leu Lys Gln Val Thr
                435                 440                 445

AAA GAA GAA ATT AAA CTT CGC CAA ATC CGC CAC TTC TAC AAA GCA GAC       1392
Lys Glu Glu Ile Lys Leu Arg Gln Ile Arg His Phe Tyr Lys Ala Asp
        450                 455                 460

CCT GAC TAC GGC CGC CGC GTT GCC GAA GGT CTT GGA TTG CCG ATT AAA       1440
Pro Asp Tyr Gly Arg Arg Val Ala Glu Gly Leu Gly Leu Pro Ile Lys
465                 470                 475                 480

AAA GAT TCT                                                            1449
Lys Asp Ser (2) INFORMATION FOR SEQ ID NO:7:

(i) SEQUENCE CHARACTERISTICS:
        (A) LENGTH: 483 amino acids
        (B) TYPE: amino acid
        (D) TOPOLOGY: linear (ii) MOLECULE TYPE: protein (xi) SEQUENCE DESCRIPTION: SEQ ID NO:7:

Met Ser Ser Asn Lys Leu Thr Thr Ser Trp Gly Ala Pro Val Gly Asp
 1               5                  10                  15

Asn Gln Asn Ser Ile Thr Ala Gly Asn Pro Gly Pro Thr Leu Ile Gln
```

```
                    20                  25                  30
Asp Val His Leu Ile Glu Lys Leu Ala His Phe Asn Arg Glu Arg Val
            35                  40                  45
Pro Glu Arg Val Val His Ala Lys Gly Ala Gly Ala His Gly Tyr Phe
        50                  55                  60
Glu Val Thr Asn Asp Met Ser Lys Tyr Thr Lys Ala Lys Val Phe Asn
 65                  70                  75                  80
Gly Val Gly Lys Arg Thr Pro Val Phe Val Arg Phe Ser Thr Val Ala
                85                  90                  95
Gly Glu Leu Gly Ser Ala Asp Thr Val Arg Asp Pro Arg Gly Phe Ala
            100                 105                 110
Val Lys Phe Tyr Thr Glu Glu Gly Asn Tyr Asp Ile Val Gly Asn Asn
        115                 120                 125
Thr Pro Ile Phe Phe Ile Arg Asp Ala Ile Lys Phe Ser Asp Phe Ile
130                 135                 140
His Thr Gln Lys Arg Asp Pro Arg Thr His Leu Ile Tyr Pro Thr Ala
145                 150                 155                 160
Met Trp Asp Phe Leu Ser Leu Ser Pro Glu Ser Leu His Gln Val Thr
                165                 170                 175
Tyr Leu Phe Gly Asp Arg Gly Ile Pro Leu Thr Tyr Arg His Met Asn
            180                 185                 190
Gly Tyr Gly Ser His Thr Phe Lys Trp Val Asn Glu Lys Gly Glu Ala
        195                 200                 205
Val Trp Val Lys Tyr His Phe Lys Thr Asn Gln Gly Val Lys Asn Met
        210                 215                 220
Asp Pro Glu Leu Ala Val Lys Ile Ala Gly Glu Asn Pro Asp Tyr His
225                 230                 235                 240
Thr Glu Asp Leu Tyr Asn Ala Ile Glu Lys Gly Asp Tyr Pro Ser Trp
                245                 250                 255
Thr Leu Tyr Val Gln Ile Met Pro Leu Glu Asp Ala Lys Thr Tyr Arg
            260                 265                 270
Phe Asn Pro Phe Asp Val Thr Lys Val Trp Ser His Lys Asp Tyr Pro
        275                 280                 285
Leu Ile Glu Val Gly Arg Met Val Leu Asn Arg Asn Pro Glu Asn Tyr
    290                 295                 300
Phe Ala Glu Val Glu Gln Ala Thr Phe Ser Pro Gly Asn Leu Val Pro
305                 310                 315                 320
Gly Val Glu Pro Ser Pro Asp Lys Ile Leu Gln Ala Arg Leu Phe Ala
                325                 330                 335
Tyr Ala Asp Ala His Arg Tyr Arg Val Gly Val Asn His Asn Leu Leu
            340                 345                 350
Pro Ile Asn Arg Pro Arg Val Glu Val Asn Asn Tyr Gln Arg Asp Gly
        355                 360                 365
Phe Met Arg Phe Asp Asn Asn Gly Gly Gly Ser Val Asn Tyr Glu Pro
    370                 375                 380
Asn Ser Phe Gly Gly Pro Thr Glu Val Pro Glu His Lys Thr Thr Pro
385                 390                 395                 400
Phe Pro Val Ser Gly Val Ala Glu Ser Val Pro Tyr Asp Asp Asp Asp
                405                 410                 415
His Tyr Thr Gln Ala Gly Asp Leu Tyr Arg Leu Met Ser Glu Glu Glu
            420                 425                 430
Lys Ala Arg Leu Val Lys Asn Ile Val Glu Ser Leu Lys Gln Val Thr
        435                 440                 445
```

```
        Lys Glu Glu Ile Lys Leu Arg Gln Ile Arg His Phe Tyr Lys Ala Asp
            450                 455                 460
        Pro Asp Tyr Gly Arg Arg Val Ala Glu Gly Leu Gly Leu Pro Ile Lys
        465                 470                 475                 480

Lys Asp Ser (2) INFORMATION FOR SEQ ID NO:8:

(i) SEQUENCE CHARACTERISTICS:
        (A) LENGTH: 1452 base pairs
        (B) TYPE: nucleic acid
        (C) STRANDEDNESS: single
        (D) TOPOLOGY: Not Relevant (ii) MOLECULE TYPE: cDNA (ix) FEATURE:
        (A) NAME/KEY: CDS
        (B) LOCATION: 1..1449

(ix) FEATURE:
        (A) NAME/KEY: mat_peptide
        (B) LOCATION: 1..1449

(xi) SEQUENCE DESCRIPTION: SEQ ID NO:8:

ATG AGT TCA AAT AAA CTG ACA ACT AGC TGG GGC GCT CCG GTT GGA GAT            48
Met Ser Ser Asn Lys Leu Thr Thr Ser Trp Gly Ala Pro Val Gly Asp
 1               5                  10                  15

AAT CAA AAC TCA ATG ACT GCC GGT TCT CGC GGA CCA ACT TTA ATT CAA            96
Asn Gln Asn Ser Met Thr Ala Gly Ser Arg Gly Pro Thr Leu Ile Gln
                20                  25                  30

GAT GTA CAT TTA CTC GAA AAA TTG GCC CAT TTC AAC CGA GAA CGT GTT           144
Asp Val His Leu Leu Glu Lys Leu Ala His Phe Asn Arg Glu Arg Val
            35                  40                  45

CCT GAA CGT GTT GTT CAC GCC AAA GGA GCA GGC GCA CAC GGA TAT TTT           192
Pro Glu Arg Val Val His Ala Lys Gly Ala Gly Ala His Gly Tyr Phe
        50                  55                  60

GAA GTG ACA AAC GAC GTA ACA AAA TAC ACG AAA GCC GCT TTC CTT TCT           240
Glu Val Thr Asn Asp Val Thr Lys Tyr Thr Lys Ala Ala Phe Leu Ser
 65                  70                  75                  80

GAA GTC GGC AAA CGC ACA CCG TTG TTC ATC CGT TTC TCA ACA GTT GCC           288
Glu Val Gly Lys Arg Thr Pro Leu Phe Ile Arg Phe Ser Thr Val Ala
                85                  90                  95

GGT GAA CTT GGC TCT GCT GAC ACA GTT CGC GAC CCG CGC GGA TTT GCT           336
Gly Glu Leu Gly Ser Ala Asp Thr Val Arg Asp Pro Arg Gly Phe Ala
            100                 105                 110

GTT AAA TTT TAT ACT GAA GAA GGA AAC TAC GAC ATC GTC GGC AAC AAT           384
Val Lys Phe Tyr Thr Glu Glu Gly Asn Tyr Asp Ile Val Gly Asn Asn
        115                 120                 125

ACG CCT GTA TTC TTT ATC CGC GAT GCG ATT AAG TTC CCT GAT TTC ATC           432
Thr Pro Val Phe Phe Ile Arg Asp Ala Ile Lys Phe Pro Asp Phe Ile
        130                 135                 140

CAT ACA CAA AAA AGA GAT CCA AAA ACA CAC CTG AAA AAC CCT ACG GCT           480
His Thr Gln Lys Arg Asp Pro Lys Thr His Leu Lys Asn Pro Thr Ala
145                 150                 155                 160

GTA TGG GAT TTC TGG TCA CTT TCA CCA GAG TCA TTG CAC CAA GTG ACA           528
Val Trp Asp Phe Trp Ser Leu Ser Pro Glu Ser Leu His Gln Val Thr
                165                 170                 175

ATC CTG ATG TCT GAC CGC GGA ATT CCT GCG ACA CTT CGC CAC ATG CAC           576
Ile Leu Met Ser Asp Arg Gly Ile Pro Ala Thr Leu Arg His Met His
            180                 185                 190

GGC TTC GGA AGC CAT ACA TTC AAA TGG ACA AAT GCC GAA CCC GAA GGC           624
```

```
              Gly Phe Gly Ser His Thr Phe Lys Trp Thr Asn Ala Glu Pro Glu Gly
                              195                 200                 205

GTA TGG ATT AAA TAT CAC TTT AAA ACA GAA CAA GGC GTG AAA AAC CTT             672
Val Trp Ile Lys Tyr His Phe Lys Thr Glu Gln Gly Val Lys Asn Leu
    210                 215                 220

GAT GTC AAT ACG GCA GCA AAA ATT GCC GGT GAA AAC CCT GAT TAC CAT             720
Asp Val Asn Thr Ala Ala Lys Ile Ala Gly Glu Asn Pro Asp Tyr His
225                 230                 235                 240

ACA GAA GAC CTT TTC AAC GCA ATC GAA AAC GGT GAT TAT CCT GCA TGG             768
Thr Glu Asp Leu Phe Asn Ala Ile Glu Asn Gly Asp Tyr Pro Ala Trp
                245                 250                 255

AAA CTA TAT GTG CAA ATC ATG CCT TTA GAA GAT GCA AAT ACG TAC CGT             816
Lys Leu Tyr Val Gln Ile Met Pro Leu Glu Asp Ala Asn Thr Tyr Arg
            260                 265                 270

TTC GAT CCG TTT GAT GTC ACA AAA GTT TGG TCT CAA AAA GAC TAC CCG             864
Phe Asp Pro Phe Asp Val Thr Lys Val Trp Ser Gln Lys Asp Tyr Pro
        275                 280                 285

TTA ATC GAG GTC GGA CGC ATG GTT CTA GAC AGA AAT CCG GAA AAC TAC             912
Leu Ile Glu Val Gly Arg Met Val Leu Asp Arg Asn Pro Glu Asn Tyr
    290                 295                 300

TTT GCA GAG GTA GAA CAA GCG ACA TTT TCA CCT GGA ACC CTC GTG CCT             960
Phe Ala Glu Val Glu Gln Ala Thr Phe Ser Pro Gly Thr Leu Val Pro
305                 310                 315                 320

GGT ATT GAT GTT TCA CCG GAT AAA ATG CTT CAA GGT CGA CTT TTT GCT            1008
Gly Ile Asp Val Ser Pro Asp Lys Met Leu Gln Gly Arg Leu Phe Ala
                325                 330                 335

TAT CAT GAT GCA CAC CGC TAC CGT GTC GGT GCA AAC CAT CAA GCG CTG            1056
Tyr His Asp Ala His Arg Tyr Arg Val Gly Ala Asn His Gln Ala Leu
                340                 345                 350

CCA ATC AAC CGC GCA CGC AAC AAA GTA AAC AAT TAT CAG CGT GAT GGG            1104
Pro Ile Asn Arg Ala Arg Asn Lys Val Asn Asn Tyr Gln Arg Asp Gly
            355                 360                 365

CAA ATG CGT TTT GAT GAT AAC GGC GGC GGA TCT GTG TAT TAC GAG CCT            1152
Gln Met Arg Phe Asp Asp Asn Gly Gly Gly Ser Val Tyr Tyr Glu Pro
        370                 375                 380

AAC AGC TTC GGC GGT CCA AAA GAG TCA CCT GAG GAT AAG CAA GCA GCA            1200
Asn Ser Phe Gly Gly Pro Lys Glu Ser Pro Glu Asp Lys Gln Ala Ala
385                 390                 395                 400

TAT CCG GTA CAA GGT ATC GCT GAC AGC GTA AGC TAC GAT CAC TAC GAT            1248
Tyr Pro Val Gln Gly Ile Ala Asp Ser Val Ser Tyr Asp His Tyr Asp
                405                 410                 415

CAC TAC ACT CAA GCC GGC GAT CTG TAT CGT TTA ATG AGT GAA GAT GAA            1296
His Tyr Thr Gln Ala Gly Asp Leu Tyr Arg Leu Met Ser Glu Asp Glu
                420                 425                 430

CGT ACC CGC CTT GTT GAA AAT ATC GTT AAT GCC ATG AAG CCG GTA GAA            1344
Arg Thr Arg Leu Val Glu Asn Ile Val Asn Ala Met Lys Pro Val Glu
            435                 440                 445

AAA GAA GAA ATC AAG CTG CGC CAA ATC GAG CAC TTC TAC AAA GCG GAT            1392
Lys Glu Glu Ile Lys Leu Arg Gln Ile Glu His Phe Tyr Lys Ala Asp
        450                 455                 460

CCT GAA TAC GGA AAA CGC GTG GCA GAA GGC CTT GGA TTG CCG ATT AAA            1440
Pro Glu Tyr Gly Lys Arg Val Ala Glu Gly Leu Gly Leu Pro Ile Lys
465                 470                 475                 480

AAA GAT TCT TAA                                                             1452
Lys Asp Ser
```

(2) INFORMATION FOR SEQ ID NO:9:

(i) SEQUENCE CHARACTERISTICS:
        (A) LENGTH: 483 amino acids (B) TYPE: amino acid
(D) TOPOLOGY: linear (ii) MOLECULE TYPE: protein (xi) SEQUENCE DESCRIPTION: SEQ ID NO:9:

```
Met Ser Ser Asn Lys Leu Thr Thr Ser Trp Gly Ala Pro Val Gly Asp
 1               5                  10                  15

Asn Gln Asn Ser Met Thr Ala Gly Ser Arg Gly Pro Thr Leu Ile Gln
            20                  25                  30

Asp Val His Leu Leu Glu Lys Leu Ala His Phe Asn Arg Glu Arg Val
        35                  40                  45

Pro Glu Arg Val Val His Ala Lys Gly Ala Gly Ala His Gly Tyr Phe
    50                  55                  60

Glu Val Thr Asn Asp Val Thr Lys Tyr Thr Lys Ala Ala Phe Leu Ser
 65                  70                  75                  80

Glu Val Gly Lys Arg Thr Pro Leu Phe Ile Arg Phe Ser Thr Val Ala
                85                  90                  95

Gly Glu Leu Gly Ser Ala Asp Thr Val Arg Asp Pro Arg Gly Phe Ala
            100                 105                 110

Val Lys Phe Tyr Thr Glu Glu Gly Asn Tyr Asp Ile Val Gly Asn Asn
        115                 120                 125

Thr Pro Val Phe Phe Ile Arg Asp Ala Ile Lys Phe Pro Asp Phe Ile
130                 135                 140

His Thr Gln Lys Arg Asp Pro Lys Thr His Leu Lys Asn Pro Thr Ala
145                 150                 155                 160

Val Trp Asp Phe Trp Ser Leu Ser Pro Glu Ser Leu His Gln Val Thr
                165                 170                 175

Ile Leu Met Ser Asp Arg Gly Ile Pro Ala Thr Leu Arg His Met His
            180                 185                 190

Gly Phe Gly Ser His Thr Phe Lys Trp Thr Asn Ala Glu Pro Glu Gly
        195                 200                 205

Val Trp Ile Lys Tyr His Phe Lys Thr Glu Gln Gly Val Lys Asn Leu
    210                 215                 220

Asp Val Asn Thr Ala Ala Lys Ile Ala Gly Glu Asn Pro Asp Tyr His
225                 230                 235                 240

Thr Glu Asp Leu Phe Asn Ala Ile Glu Asn Gly Asp Tyr Pro Ala Trp
                245                 250                 255

Lys Leu Tyr Val Gln Ile Met Pro Leu Glu Asp Ala Asn Thr Tyr Arg
            260                 265                 270

Phe Asp Pro Phe Asp Val Thr Lys Val Trp Ser Gln Lys Asp Tyr Pro
        275                 280                 285

Leu Ile Glu Val Gly Arg Met Val Leu Asp Arg Asn Pro Glu Asn Tyr
    290                 295                 300

Phe Ala Glu Val Glu Gln Ala Thr Phe Ser Pro Gly Thr Leu Val Pro
305                 310                 315                 320

Gly Ile Asp Val Ser Pro Asp Lys Met Leu Gln Gly Arg Leu Phe Ala
                325                 330                 335

Tyr His Asp Ala His Arg Tyr Arg Val Gly Ala Asn His Gln Ala Leu
            340                 345                 350

Pro Ile Asn Arg Ala Arg Asn Lys Val Asn Asn Tyr Gln Arg Asp Gly
        355                 360                 365

Gln Met Arg Phe Asp Asp Asn Gly Gly Gly Ser Val Tyr Tyr Glu Pro
    370                 375                 380
```

```
Asn Ser Phe Gly Gly Pro Lys Glu Ser Pro Glu Asp Lys Gln Ala Ala
385                 390                 395                 400

Tyr Pro Val Gln Gly Ile Ala Asp Ser Val Ser Tyr Asp His Tyr Asp
            405                 410                 415

His Tyr Thr Gln Ala Gly Asp Leu Tyr Arg Leu Met Ser Glu Asp Glu
        420                 425                 430

Arg Thr Arg Leu Val Glu Asn Ile Val Asn Ala Met Lys Pro Val Glu
            435                 440                 445

Lys Glu Glu Ile Lys Leu Arg Gln Ile Glu His Phe Tyr Lys Ala Asp
        450                 455                 460

Pro Glu Tyr Gly Lys Arg Val Ala Glu Gly Leu Gly Leu Pro Ile Lys
465                 470                 475                 480

Lys Asp Ser
```

(2) INFORMATION FOR SEQ ID NO:10:

(i) SEQUENCE CHARACTERISTICS:
    (A) LENGTH: 3466 base pairs
    (B) TYPE: nucleic acid
    (C) STRANDEDNESS: single
    (D) TOPOLOGY: Not Relevant (ii) MOLECULE TYPE: cDNA (xi) SEQUENCE DESCRIPTION: SEQ ID NO:10:

```
CTGCAGCCTT TCTTTAAAAG AGTCGAAAGC CAGGCTTTTA ATATTTAAAT CACCATAATT      60

ACTCTGTATT AAGTTTGTAG AAAACATCTC CCGCCTCATA TTGTTAACAA AATTATTATC     120

TCATTTAAAT CTAAGTCATT TACAATATAA GTTTAAGAGC GACGCCACAG GATGAACTAT     180

CAAAAATAGC TCATCATGAT TAGCAAAACT TAACCATTTT AAAATAAATA AACAATTAAA     240

GAAAAAGAT CACTTATTTA TAGCAATAGA TCGTCAAAGG CAGCTTTTTG TTACAGGTGG      300

TTTGAATGAA TGTAGCAACG AAATACAGAA TTTCAGGTCA TGTAACTCCC GGCAAACCGG     360

GAGGTATGTA ATCCTTACTC AGTCACTTCC CCTTCCTGGC GGATCTGATT TGCCCAACGT     420

TGGGCAGATT CAGGCACAGT AAACGCCGGT GAGCGCAGAA ATGACTCTCC CATCAGTACA     480

AACGCAACAT ATTTGCCACG CAGCATCCAG ACATCACGAA ACGAATCCAT CTTTATCGCA     540

TGTTCTGGCG GCGCGGGTTC CGTGCGTGGG ACATAGCTAA TAATCTGGCG GTTTTGCTGG     600

CGGAGCGGTT TCTTCATTAC TGGCTTCACT AAACGCATAT TAAAAATCAG AAAAACTGTA     660

GTTTAGCCGA TTTAGCCCCT GTACGTCCCG CTTTGCGTGT ATTTCATAAC ACCGTTTCCA     720

GAATAGTCTC CGAAGCGGGA TCTGGCTGGT GGTCTATAGT TAGAGAGTTT TTTGACCAAA     780

ACAGCGGCCC TTTCAGTAAT AAATTAAGGA GACGAGTTCA ATGTCGCAAC ATAACGAAAA     840

GAACCCACAT CAGCACCAGT CACCACTACA CGATTCCAGC GAAGCGAAAC CGGGGATGGA     900

CTCACTGGCA CCTGAGGACG GCTCTCATCG TCCAGCGGCT GAACCAACAC CGCCAGGTGC     960

ACAACCTACC GCCCCAGGGA GCCTGAAAGC CCCTGATACG CGTAACGAAA AACTTAATTC    1020

TCTGGAAGAC GTACGCAAAG GCAGTGAAAA TTATGCGCTG ACCACTAATC AGGGCGTGCG    1080

CATCGCCGAC GATCAAAACT CACTGCGTGC CGGTAGCCGT GGTCCAACGC TGCTGGAAGA    1140

TTTTATTCTG CGCGAGAAAA TCACCCACTT TGACCATGAG CGCATTCCGG AACGTATTGT    1200

TCATGCACGC GGATCAGCCG CTCACGGTTA TTTCCAGCCA TATAAAAGCT TAAGCGATAT    1260

TACCAAAGCG GATTTCCTCT CAGATCCGAA CAAAATCACC CCAGTATTTG TACGTTTCTC    1320

TACCGTTCAG GGTGGTGCTG GCTCTGCTGA TACCGTGCGT GATATCCGTG GCTTTGCCAC    1380
```

```
                                                                -continued

CAAGTTCTAT ACCGAAGAGG GTATTTTTGA CCTCGTTGGC AATAACACGC CAATCTTCTT    1440

TATCCAGGAT GCGCATAAAT TCCCCGATTT TGTTCATGCG GTAAAACTAG AACCGCACTG    1500

GGCAATTCCA CAAGGGCAAA GTGCCCACGA TACTTTCTGG GATTATGTTT CTCTGCAACC    1560

TGAAACTCTG CACAACGTGA TGTGGGCGAT GTCGGATCGC GGCATCCCCC GCAGTTACCG    1620

CACCATGGAA GGCTTCGGTA TTCACACCTT CCGCCTGATT AATGCCGAAG GAAGGCAAC     1680

GTTTGTACGT TTCCACTGGA AACCACTGGC AGGTAAAGCC TCACTCGTTT GGGATGAAGC    1740

ACAAAAACTC ACCGGACGTG ACCCGGACTT CCACCGCCGC GAGTTGTGGG AAGCCATTGA    1800

AGCAGGCCAT TTTCCGGAAT ACGAACTGGG CTTCCAGTTG ATTCCTGAAG AAGATGAATT    1860

CAAGTTCGAC TTCGATCTTC TCGATCCAAC CAAACTTATC CCGGAAGAAC TGGTGCCCGT    1920

TCAGCGTGTC GGCAAAATGG TGCTCAATCG CAACCCGGAT AACTTCTTTG CTGAAAACGA    1980

ACAGGCGGCT TTCCATCCTG GGCATATCGT GCCGGGACTG GACTTCACCA ACGATCCGCT    2040

GTTGCAGGGA CGTTTGTTCT CCTATACCGA TACACAAATC AGTCGTCTTG GTGGGCCGAA    2100

TTTCCATGAG ATTCCGATTA ACCGTCCGAC CTGCCCTTAC CATAATTTCC AGCGTGACGG    2160

CATGCATCGC ATGGGGATCG ACACTAACCC GGCGAATTAC GAACCGAACT CGATTAACGA    2220

TAACTGGCCG CGCGAAACAC CGCCGGGGCC GAAACGCGGC GGTTTTGAAT CATACCAGGA    2280

GCGCGTGGAA GGCAATAAAG TTCGCGAGCG CAGCCCATCG TTTGGCGAAT ATTATTCCCA    2340

TCCGCGTCTG TTCTGGCTAA GTCAGACGCC ATTTGAGCAG CGCCATATTG TCGATGGTTT    2400

CAGTTTTGAG TTAAGCAAAG TCGTTCGTCC GTATATTCGT GAGCGCGTTG TTGACCAGCT    2460

GGCGCATATT GATCTCACTC TGGCCCAGGC GGTGGCGAAA AATCTCGGTA TCGAACTGAC    2520

TGACGACCAG CTGAATATCA CCCCACCTCC GGACGTCAAC GGTCTGAAAA AGGATCCATC    2580

CTTAGTTTGT ACGCCATTCC TGACGGTGAT GTGAAAGGTC GCGTGGTAGC GATTTTTACT    2640

TATTGATGAA GTGAGATCGG CAGACCTTCT GGCCATTCTC AAGGCGCTGA AGGCCAAAGG    2700

CGTTCATGCC AAACTGCTCT ACTCCCGAAT GGGTGAAGTG ACTGCGGATG ACGGAACGGT    2760

GTTGCCTATA GCCGCTACCT TTGCCGGTGC ACCTTCGCTG ACGGTCGATG CGGTCATTGT    2820

CCCTTGCGGC AATATCGCGG ATATCGCTGA CAACGGCGAT GCCAACTACT ACCTGATGGA    2880

AGCCTACAAA CACCTTAAAC CGATTGCGCT GGCGGGTGAC GCGCGCAAGT TTAAAGCAAC    2940

AATCAAGATC GCTGACCAGG GTGAAGAAGG GATTGTGGAA GCTGACAGCG CTGACGGTAG    3000

TTTTATGGAT GAACTGCTAA CGCTGATGGC AGCACACCGC GTGTGGTCAC GCATTCCTAA    3060

GATTGACAAA ATTCCTGCCT GATGGGAGCG CGCAATTGCG CCGCCTCAAT GATTTACATA    3120

GTGCGCTTTG TTTATGCCGG ATGCGCGTGA ACGCCTTATC CGGCCTACAA AACTGTGCAA    3180

ATTCAATATA TTGCAGGAAA CACGTAGGCC TGATAAGCGA AGCCATCAGG CAGTTTTGCG    3240

TTTGTCAGCA GTCTCAAGCG GCGGCAGTTA CGCCGCCTTT GTAGGAATTA ATCGCCGGAT    3300

GCAAGGTTCA CGCCGATCTG GCAAACATCC TCACTTACAC ATCCCGATAA CTCCCCAACC    3360

GATAACCACG CTGAGCGATA GCACCTTTCA ACGACGCTGA TGTCAACACA TCCAGCTCCG    3420

TTAAGCGTGG GAAACAGTAA GCACTCTGAC GGATAGTATT ATCGAT                  3466
```

What is claimed is:

1. An isolated catalase gene comprising the sequence depicted in SEQ ID NO: 6 and the degenerate sequences thereof.

2. The isolated gene according to claim 1 that is derived from *Bacillus thermogludosasius*.

3. A process for preparing a *B. thermoglucosdasius*-derived catalase usng genetic technology, which comprises:

(a) constructing a recombinant plasmid by inserting a gene encoding a *B. thermoglucosdasius*-derived catalase into an expression vector containing a proper transcription promoter;

(b) transforming proper host cells with said recombinant plasmid;
(c) culturing said transformant cells under conditions suitable for the transformant cells to express the catalase gene; and
(d) purifying the catalase protein expressed.

4. The process according to claim 3, wherein the gene encoding the catalase is the catalase gene comprising the sequence depicted in SEQ ID NO: 6 derived from *Bacillus thermolucosdasius*.

5. The process according to claim 3, wherein said host cells are bacterial.

6. The process according to claim 5, wherein said host cell is an *E. coli* cell.

7. A recombinant plasmid for expressing a *B. theroglucosdasius*-derived catalase, which plasmid is constructed by inserting the gene encoding the catalase into an expression vector.

8. The recombinant plasmid according to claim 7, wherein said expression vector is useful in an *E. coli* expression system.

9. The recombinant plasmid according to claim 7 wherein the gene encoding the *B. thermoglucosdasius*-derived catalase is the catalase gene comprising the sequence depicted in SEQ ID NO: 6 derived from *Bacillus thermoglucosdasius*.

10. The recombinant plasmid according to claim 9 which is pET 20b/katTG.

11. A transformant cell for expressing a *B. thermoglucosdasius*-derived catalase, which is a host cell transformed with the recombinant plasmid according to claim 7.

12. The transformant cell according to claim 11, wherein said host cell is an *E. coli* cell.

13. A transformant cell for expressing a *B. thermoglcosdasius*-derived catalase, which transformed cell is a host cell transformed with the recombinant plasmid according to claim 9.

14. A transformant cell for expressing a *B. theroglucosdasius*-dernved catalase, which transformed cell is a host cell transformed with the recombinant plasmid according to claim 10.

15. The transformant cell according to claim 13, wherein said host cell is an *E. coli* cell.

16. An isolated catalase comprising the sequence depicted in SEQ ID NO: 8 and the functional fragments thereof.

17. A composition for use in destroying hydrogen peroxide present in a residual disinfectant, which composition comprises an effective amount of a *B. thermoglucosdasius* catalase.

18. The composition according to claim 17 wherein the catalase is a catalase comprising the sequence depicted in SEQ ID NO: 8 and functional fragments thereof.

19. A composition according to claim 17 wherein the hydrogen peroxide is present in residual disinfectant remaining on a contact lens.

* * * * *